(12) United States Patent
Sonar et al.

(10) Patent No.: US 8,816,334 B2
(45) Date of Patent: Aug. 26, 2014

(54) N-TYPE MATERIALS AND ORGANIC ELECTRONIC DEVICES

(75) Inventors: Prashant Sonar, Singapore (SG); Richard Yee Cheong Shin Koy Sien, Singapore (SG); Zhikuan Chen, Singapore (SG); Kok Haw Ong, Singapore (SG); Ging Meng Ng, Singapore (SG); Achmad Zen, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 297 days.

(21) Appl. No.: 13/503,267

(22) PCT Filed: Oct. 22, 2009

(86) PCT No.: PCT/SG2009/000393
§ 371 (c)(1),
(2), (4) Date: Aug. 20, 2012

(87) PCT Pub. No.: WO2011/049531
PCT Pub. Date: Apr. 28, 2011

(65) Prior Publication Data
US 2012/0298976 A1    Nov. 29, 2012

(51) Int. Cl.
    *H01L 35/24*    (2006.01)
(52) U.S. Cl.
    USPC .................................. 257/40; 257/E51.001
(58) Field of Classification Search
    USPC .......................................... 257/40, E51.001
    See application file for complete search history.

(56) References Cited

U.S. PATENT DOCUMENTS

| 7,223,484 B2 | 5/2007 | Stössel et al. |
| 2006/0081839 A1 | 4/2006 | Jeong et al. |
| 2006/0113527 A1 | 6/2006 | Han et al. |
| 2009/0032106 A1 | 2/2009 | Sellinger et al. |

FOREIGN PATENT DOCUMENTS

JP    2009-158921 A    7/2009

*Primary Examiner* — Anthony Ho
(74) *Attorney, Agent, or Firm* — Choate, Hall & Stewart LLP; Charles E. Lyon

(57) ABSTRACT

There is presently provided organic compounds of formula I, n-type acceptor materials derived from such compounds and devices comprising such n-type acceptor materials.

$$(A_n\text{-}D_p)_r\text{-}A_n \qquad \qquad \text{I}$$

12 Claims, 4 Drawing Sheets

N-TYPE MATERIALS AND ORGANIC ELECTRONIC DEVICES

PRIORITY CLAIM

This application is a national phase application under 35 USC §371 of PCT International Application No. PCT/SG2009/000393 (published PCT Application No. WO 2011/049531 A1), filed Oct. 22, 2009, the contents of which are hereby incorporated by reference in their entirety for all purposes.

FIELD OF THE INVENTION

The present invention relates to organic compounds, n-type acceptor material derived from such compounds and devices comprising such n-type acceptor material.

BACKGROUND OF THE INVENTION

Organic light-emitting diodes (OLEDs), organic field-effect transistors (OFETs), and organic solar cells (also referred to as organic photovoltaics or OPVs) based on organic molecules have been extensively studied. Such devices are becoming increasingly popular due to their low-cost processing, relatively simple packaging, and compatibility with flexible substrates.

More specifically, OPVs come with the promise of efficient conversion of sunlight into direct usable electrical energy at a much lower cost than the traditional silicon based solar cells.

It is known that for efficient energy conversion in OPVs, a mixture of at least two (sometimes more) organic materials are needed: at least one material that can act as an electron donor (p-type) and at least one material that can act as electron acceptor (n-type).

Materials research in OPVs since the mid-1990s has focused primarily on the development of donor materials. As a result, there are many more organic donor materials commercially available than organic acceptor materials. For example, the most widely investigated organic semiconductors are donor materials based on aromatic amines and thiophene materials (Katz et al., *Acc. Chem. Res.* 2001, 34, 359; Chan and Ng, *Prog. Polym. Sci.* 1998, 23, 1167; Y. F. Li, Y. P. Zhou, *Adv. Mater.* 2008, 20, 2952; and Thelakkat, *Macromol. Mater. Eng.* 2002, 287, 442).

In contrast, research in electron acceptors has substantially lagged behind. Work in this area has primarily focussed on perylene and fullerene materials, which in general are relatively difficult to work with in terms of synthesis of the materials. (Greenham, et al., *Nature* 1993, 365, 628; Kulkarni et al., *Chem. Mater.* 2004, 16, 4556; and Hughes and Bryce, *J. Mater. Chem.* 2005, 15, 94). The chemistry of these compounds is relatively well known, with little room for new developments. Furthermore, production of these materials tends to be very expensive, especially in the case of fullerene based materials. Perylenes are typically insoluble, meaning that often only vacuum deposition of these compounds is possible. Since the mid-1990s, fullerene compounds have been optimized for use in solution processable organic solar cells, providing power conversion efficiencies in the range of 2-5% when combined with selected commercial donor materials. Despite this, fullerenes tend to have low absorption coefficients in the visible range, are difficult to synthesize, and have low open circuit voltage in blend devices.

Accordingly, there is a need for production of alternative n-type organic materials useful for production of efficient electronic devices, including OPVs.

SUMMARY OF THE INVENTION

The invention relates to organic compounds that can be used as acceptor materials in organic devices, including organic photovoltaic devices.

The compounds of the invention incorporate alternating blocks of electron accepting groups and electron donating groups, and are terminated at each end with a block of electron accepting groups.

The compounds of the invention may exhibit strong absorption in the visible region and thus may serve as n-type materials that allow for tuning of light absorption range and HOMO/LUMO energy levels, depending on the particular electron accepting groups and electron donating groups incorporated into the compounds.

The compounds thus may be useful in organic solar cells, also known as organic photovoltaic devices, and may allow for production of organic photovoltaic devices at lower cost than traditional silicon-based solar cells, even when using a flexible substrate.

Thus, according to one aspect of the invention, there is provided a compound of formula I:

$$(A_n\text{-}D_p)_r\text{-}A_n \qquad \qquad I$$

wherein each A is an independently selected conjugated electron withdrawing aromatic or heteroaromatic group having from 5 to 50 backbone atoms, each A optionally substituted with one or more electron withdrawing substituents or electron donating substituents, provided that even when substituted the electronic character of each A is electron withdrawing and provided that A is not fluorenonyl; each D is an independently selected ethenylene group, ethynylene group or a conjugated electron donating aromatic or heteroaromatic group having from 5 to 50 backbone atoms; each D being optionally substituted with one or more electron donating substituents or electron withdrawing substituents provided that even when substituted the electronic character of each D is electron donating; r is an integer having a value of 2 or greater; and each n is independently an integer from 1 to 20 and each p is independently an integer from 1 to 10.

In formula I, each A may be independently one of A1 to A31 and each A may optionally be substituted:

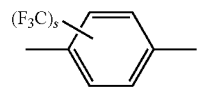

A1

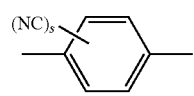

A2

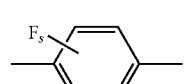

A3

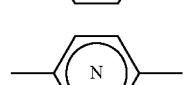

A4

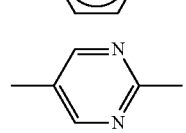

A5

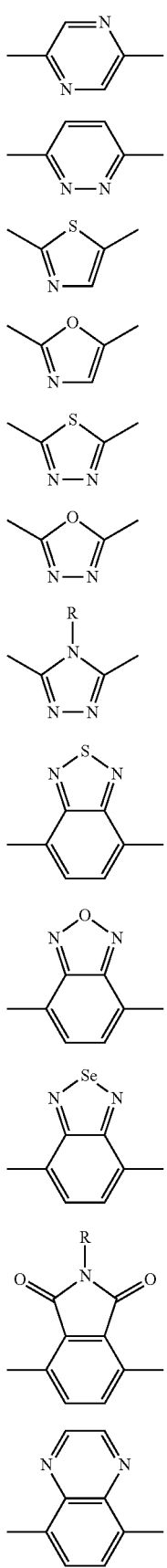
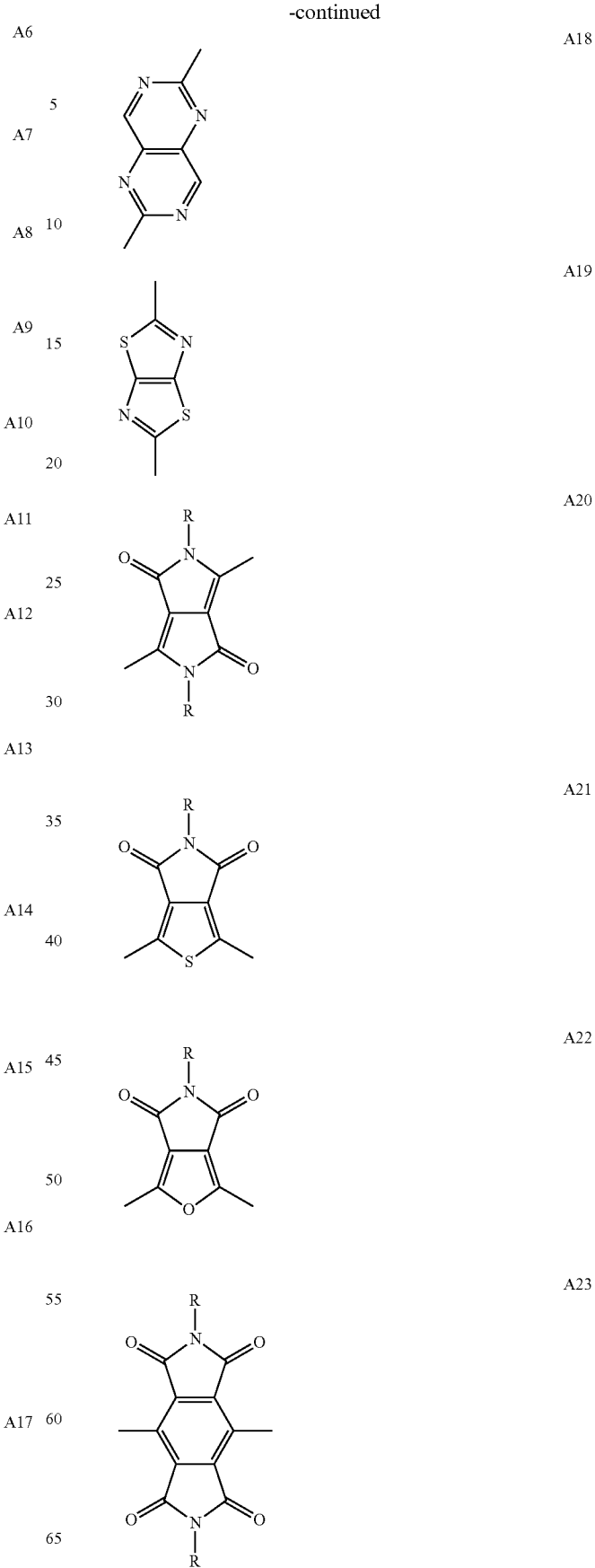

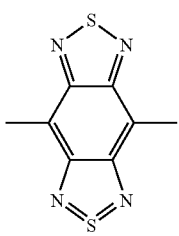

A24

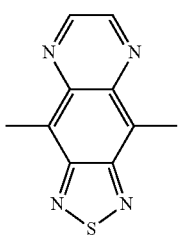

A25

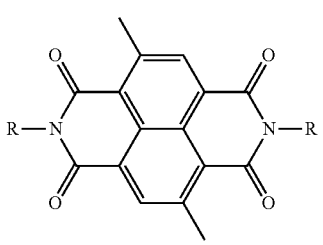

A26

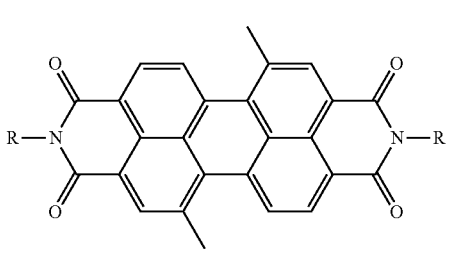

A27

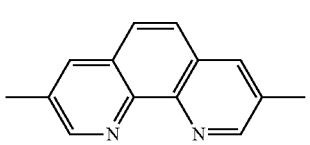

A28

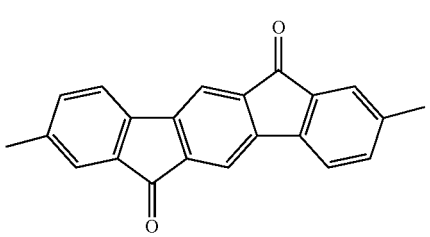

A29

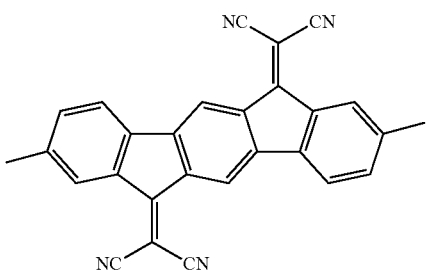

A30

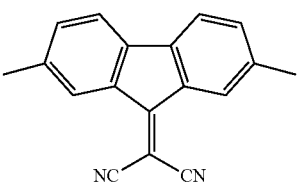

A31 wherein s is an integer from 1 to 5; and each R is independently H, straight or branched alkyl, straight or branched alkenyl, straight or branched alkynyl, straight or branched heteroalkyl provided that the heteroatom is not bonded to N, alkaryl, alkheteroaryl, heteroalkaryl, heteroalkheteroaryl, aralkyl, arheteroalkyl, heteroaralkyl, or heteroarheteroalkyl.

In formula I, each D may be independently ethenylene, ethynylene or one of D1 to D21 and each D may optionally be substituted:

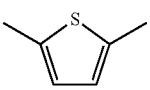

D1

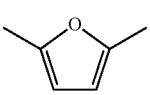

D2

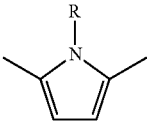

D3

D4

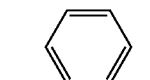

D5

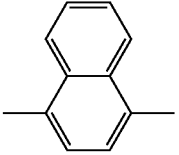

D6

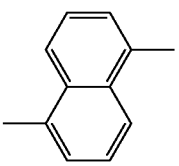

D7

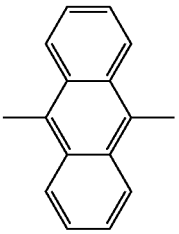

-continued

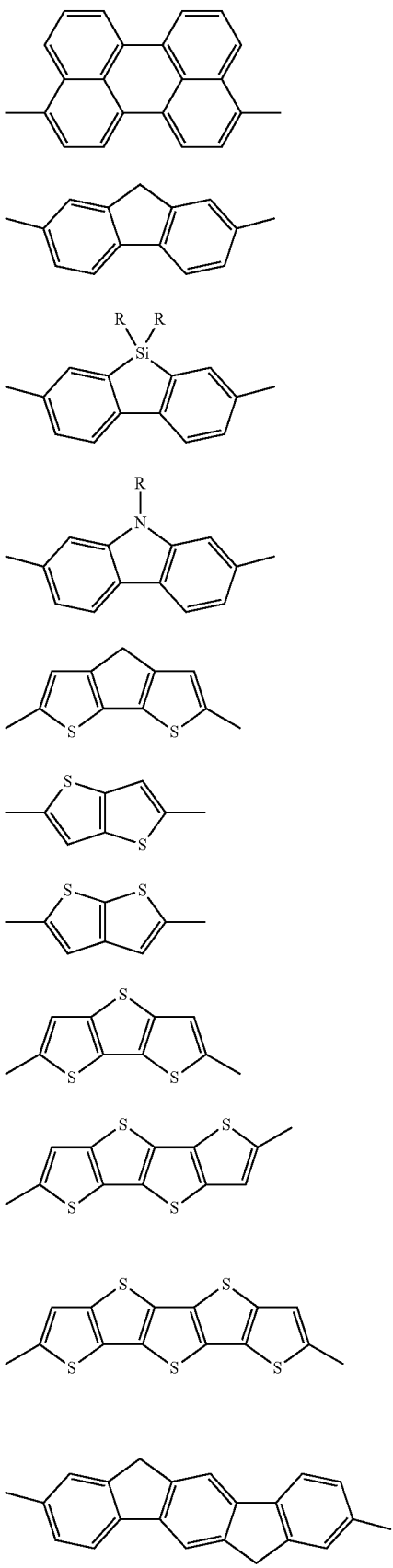

D8
D9
D10
D11
D12
D13
D14
D15
D16
D17
D18

-continued

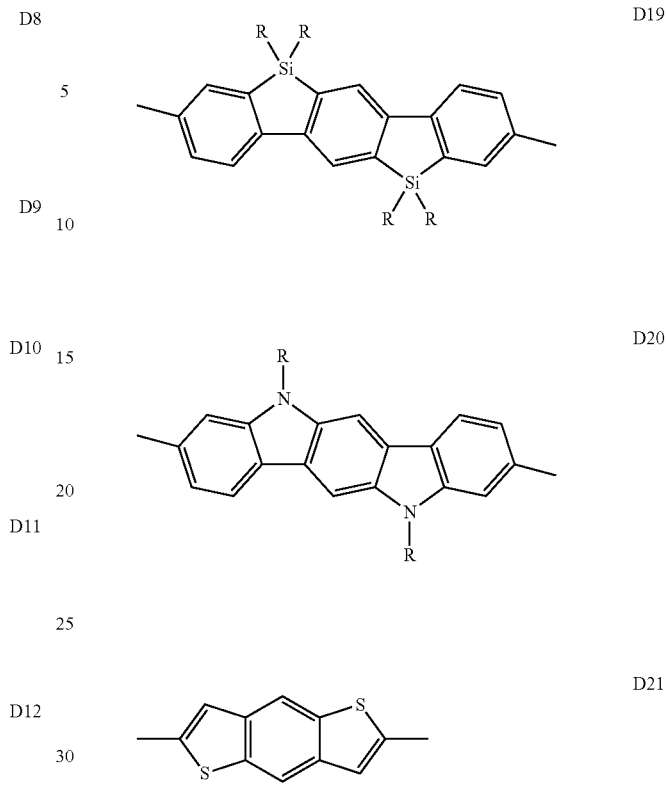

D19
D20
D21 wherein s is an integer from 1 to 5; and each R is independently H, straight or branched alkyl, straight or branched alkenyl, straight or branched alkynyl, straight or branched heteroalkyl provided that the heteroatom is not bonded to N or Si, alkaryl, alkheteroaryl, heteroalkaryl, heteroalkheteroaryl, aralkyl, arheteroalkyl, heteroaralkyl, or heteroarheteroalkyl.

In certain embodiments, each A may independently be optionally substituted by one or more halo, fluoroalkyl, perfluoroalkyl, carboxyl, cyano, ammonio, nitro, thionyl, sulfonyl, amido linked to the backbone through the oxygen, pyridinium, phosphonium, pyridyl, thiazolyl, oxadiazolyl, triazolyl, alkoxyl, alkylthio, amino, hydroxyl, amido connected to the backbone through the nitrogen, carboxyl connected to the backbone through the oxygen, phenyl, naphthyl, thienyl, furyl, pyrrolyl, carbazolyl, alkyl, alkenyl or alkynyl or any combination thereof, provided that when substituted the electronic character of each A is electron accepting.

As well, each D may independently be optionally substituted with one or more alkoxyl, alkylthio, amino, hydroxyl, amido connected to the backbone through the nitrogen, carboxyl connected to the backbone through the oxygen, phenyl, naphthyl, thienyl, furyl, pyrrolyl, carbazolyl, alkyl, alkenyl, alkynyl, halo, fluoroalkyl, perfluoroalkyl, carboxyl, cyano, ammonio, nitro, thionyl, sulfonyl, amido linked to the backbone through the oxygen, pyridinium, phosphonium, pyridyl, thiazolyl, oxadiazolyl or triazolyl or any combination thereof, provided that when substituted the electronic character of each D is electron donating.

In particular embodiments, compounds of the invention include each of N-1, N-2, N-3, N-4, N-5, N-6, N-7, N-8, N-9, N-10 and N-11:

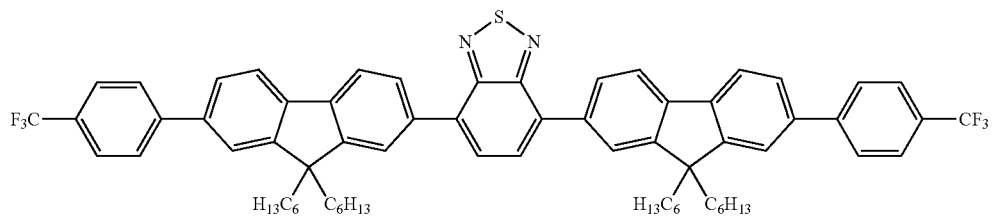
N-1
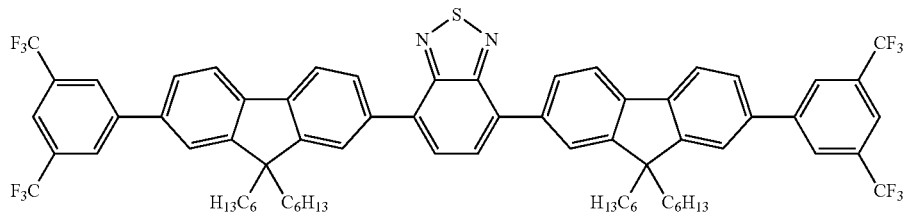
N-2
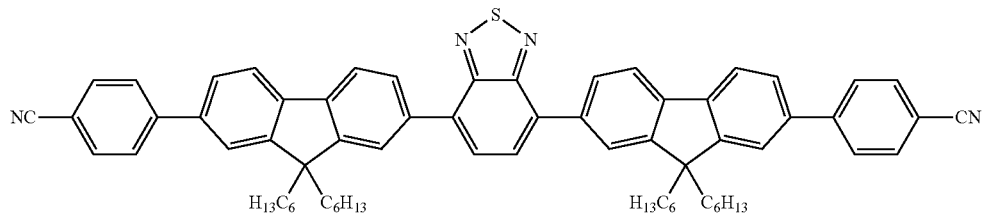
N-3
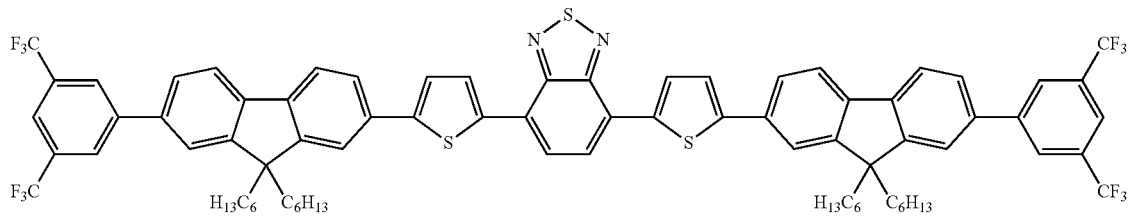
N-4
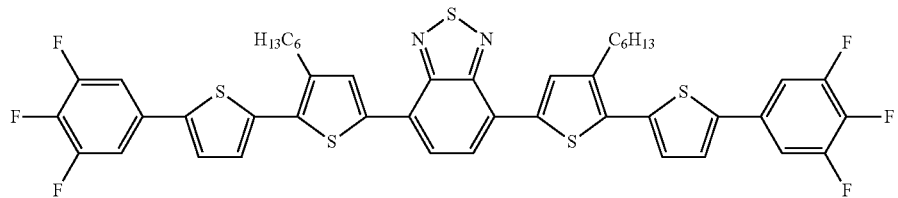
N-5
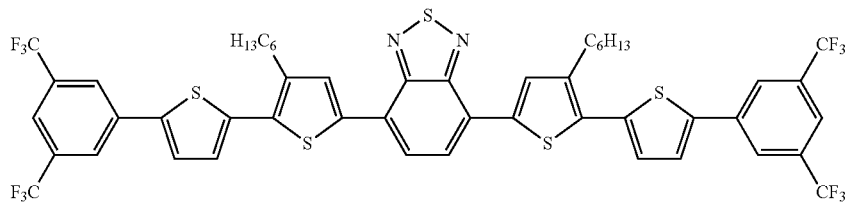
N-6
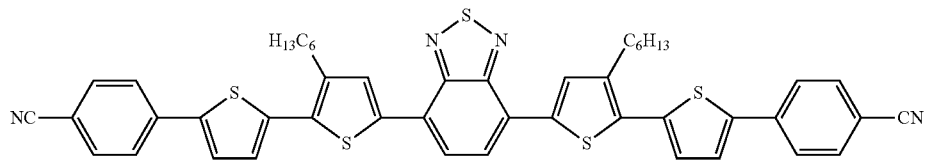
N-7

-continued

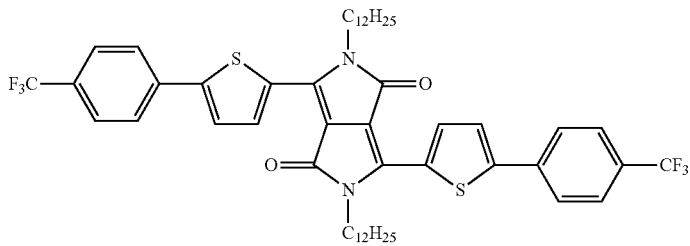

N-8

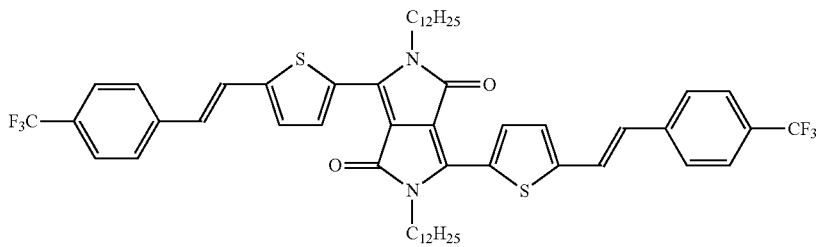

N-9

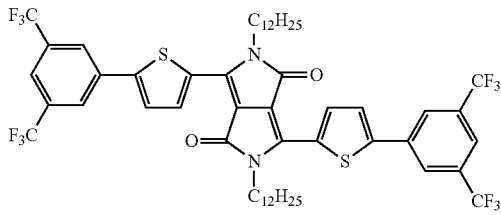

N-10

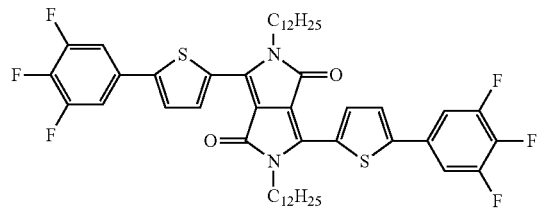

N-11

According to another aspect of the invention, there is provided a thin film comprising a compound as described herein.

The thin film may further comprise an electron donor material, which may be regioregular poly(3-hexylthiophene-2,5-diyl) (P3HT), regioregular poly(3-ocylthiophene-2,5-diyl) (P3OT), regioregular poly(quarterthiphene) (PQT), a-poly(phenylene ethynylene)-poly(phenylene vinylene) (A-PPE-PPV), poly[2-methoxy-5-(2'-ethyl-hexyloxy)-1,4-phenylene vinylene] (MEH-PPV), poly[2-methoxy-5-(3,7-dimethyloctyloxy)-1,4-phenylenevinylene] (MDMO-PPV), poly(9,9-dihexyl-fluoren-2,7-diyl-alt-bithiophen-2,5'-diyl), poly(N-alkyl-carbazo-2,7-diyl-alt-4,7-dithienyl-2,1,3-benzothiadiazo-2,5"-diyl), poly[2,6-(4,4-bis(2-ethylhexyl)-4H-cyclopenta[2,1-b:3,4-b']dithiophene)-alt-4,7-(2,1,3-benzothiadiazole)] (PCPDTBT), poly(9,9-dioctyl-silafluoren-2,7-diyl-alt-4,7-dithienyl-2,1,3-benzothiadiazo-2,5"-diyl), or poly[2,6-(4,4-bis(2-ethylhexyl)-4H-cyclopenta[2,1-b:3,4-b]dithiophenesilole)-alt-4,7-(2,1,3-benzothiadiazole)].

In particular embodiments, the donor material comprises P3HT.

In another aspect of the present invention, there is provided a device comprising an anode, a cathode and an electron acceptor material comprising a compound as described herein, the electron acceptor material disposed between the anode and the cathode.

The electron acceptor material may be included in a photoactive layer. The photoactive layer may further comprise an electron donor material, including as described above.

The device may also further comprise a smoothing layer disposed between the photoactive layer and the anode, or between the photoactive layer and the cathode.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
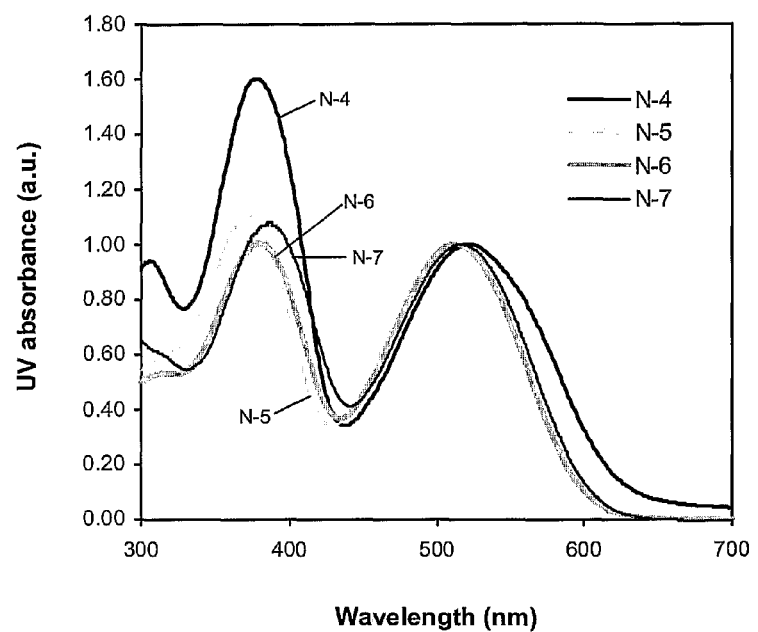
FIG. 1 is a UV absorption spectra from 300 nm to 700 nm for compounds N-4 to N-7 in toluene.

Presented here are n-type conjugated compounds that may be used as acceptor type materials, and organic devices incorporating such compounds. The compounds may be easily synthesized and may be solution processable. Accordingly, organic devices incorporating these compounds may be easily manufactured, including using solution-based techniques such as inkjet printing, dip and/or spin coating, and screen printing, to name a few.

The compounds described herein contain alternating blocks of aromatic or heteroaromatic acceptor groups (A groups, also referred to as electron withdrawing groups or electron acceptor groups), which blocks are referred to as acceptor blocks, and blocks of donor groups (D groups, also referred to as electron donating groups), which blocks are referred to as donor blocks, conjugated along the compound backbone. Each donor group is an ethenylene group, an ethynylene group, an electron donating aromatic group or an electron donating heteroaromatic group. The described compounds terminate at each end with an acceptor block, thus resulting in a compound with more acceptor blocks than donor blocks, providing the compound with an overall acceptor character, or n-type character.

An aromatic group is a cyclic group having $4n+2$ π electrons, where n is an integer equal to or greater then 0. As used herein, "aromatic" is used interchangeably with "aryl" to refer to an aromatic group, regardless of the valency of the aromatic group. Thus, aryl refers to monovalent aromatic groups, bivalent aromatic groups and higher multivalent aromatic groups. Any aromatic group may be optionally substituted.

A heteroaromatic group is an aromatic group containing one or more heteroatoms in the backbone, such as N, O, S, Se, Si or P, for example. As used herein, "heteroaromatic" is used interchangeably with "heteroaryl", and a heteroaryl group refers to monovalent aromatic groups, bivalent aromatic groups and higher multivalent aromatic groups containing one or more heteroatoms. Any heteroaromatic group may be optionally substituted.

It will be appreciated that an unsubstituted terminal aromatic or heteroaromatic group (also referred to as end-cap groups; i.e. at an end of a molecule that is formed from linking of multiple aromatic and/or heteroaromatic groups) will be monovalent and that an unsubstituted interior aromatic or heteroaromatic group (i.e. within a chain and not at an end of a molecule formed from linking of multiple aromatic and/or heteroaromatic groups) will be at least divalent.

As used herein when describing either electron withdrawing (i.e. accepting) or electron donating character of a particular aromatic or heteroaromatic group, such terms are used relative to the reference group of an unsubstituted phenyl group, either monovalent or divalent depending on whether the relevant group is a terminal group or falls within the backbone chain. Benzene is weakly electron donating, and thus electron donating aromatic or heteroaromatic groups described herein have equivalent or greater electron donating character as compared to a phenyl group. In contrast, electron withdrawing (electron accepting) aromatic or heteroaromatic groups described herein have less electron donating character as compared to a phenyl group. Thus, when a given aromatic or heteroaromatic group is conjugated to a phenyl group, if the pi electron cloud of the phenyl group moves toward the given aromatic or heteroaromatic group, the group is considered to be electron withdrawing; otherwise, the group is considered to be electron donating. Conventional methods and techniques can be used to determine whether a pi electron cloud of a phenyl group moves toward a given aromatic or heteroaromatic group, including electrophilic substitution reactions, or theoretical calculations of electron density.

An ethenylene group is a bivalent —CH=CH— group in which the two carbons are connected by a double bond. Any ethenylene group may have either or both hydrogens optionally substituted.

An ethynylene group is a bivalent —C≡C— group in which the two carbons are connected by a triple bond.

The term "conjugated" as used herein in reference to the backbone of a molecule refers to a molecule having two or more double and/or triple bonds in the main chain of the molecule, each double or triple bond being separated from the next consecutive double or triple bond by a single bond so that π orbitals overlap not only across the double or triple bond, but also across adjacent single bonds located between adjacent double and/or triple bonds. The present compounds are composed of aromatic groups, heteroaromatic groups, ethenylene groups and/or ethenylene groups connected to each other by single bonds. Thus, the double or triple bonds along the backbone will be contributed by aromatic groups, heteroaromatic groups, ethenylene groups and/or ethynylene groups whereas some single bonds along the backbone will be contributed by aromatic or heteroaromatic groups and some single bonds will connect one aromatic, heteroaromatic group, ethenylene group or ethynylene group to the next.

In order to provide sufficient acceptor character, the compounds have at least five alternating acceptor (A) and donor (D) blocks along the backbone, beginning and ending with an A block.

It should be noted that for any list of possible elements or features provided in this specification, any subset falling within a given list is also intended.

Thus, the compounds have the general formula I in which r has a value of 2 or greater:

$$(A_n\text{-}D_p)_r\text{-}A_n$$

Each A in formula I is an independently selected conjugated electron withdrawing aromatic or heteroaromatic group having from 5 to 50 backbone atoms, with the stipulation that A is not fluorenonyl. Each A may be optionally substituted with one or more substituents provided that when substituted the electronic character of each A is electron accepting, as described above. Thus, substituents include electron withdrawing substituents as well as electron donating substituents.

In certain embodiments, each A is independently one of the following groups, any of which may be further substituted where appropriate:

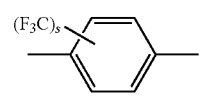
A1

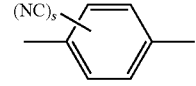
A2

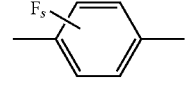
A3

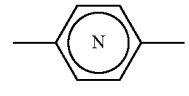
A4

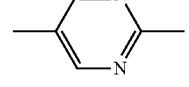
A5

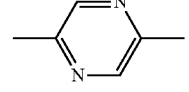
A6

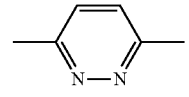
A7

-continued
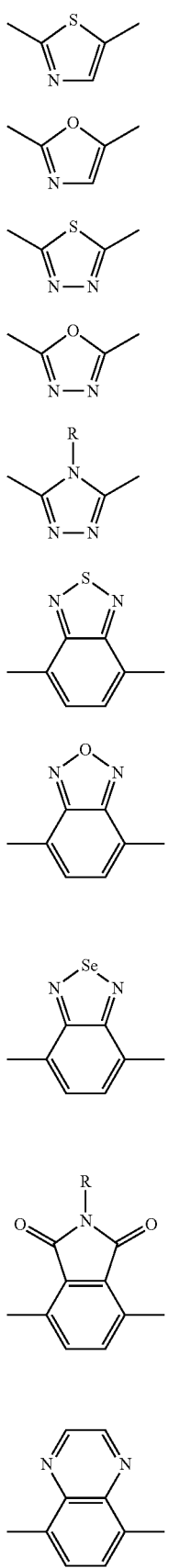
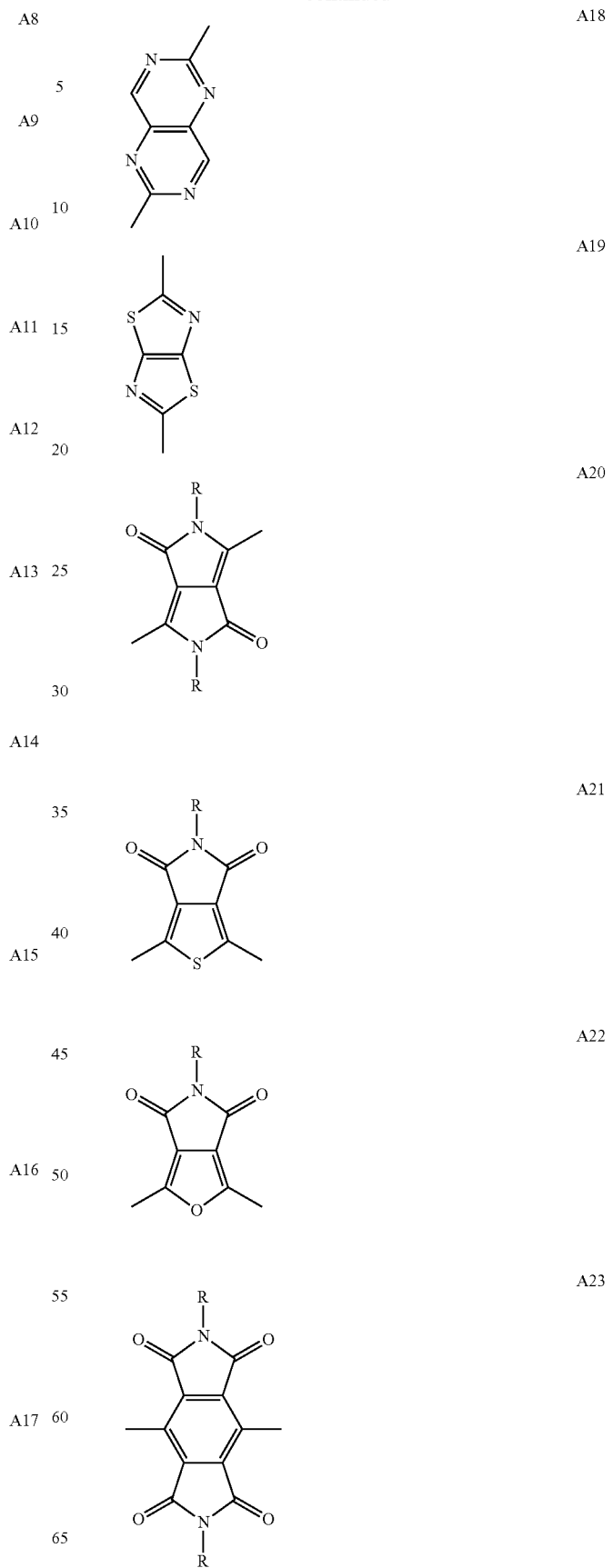

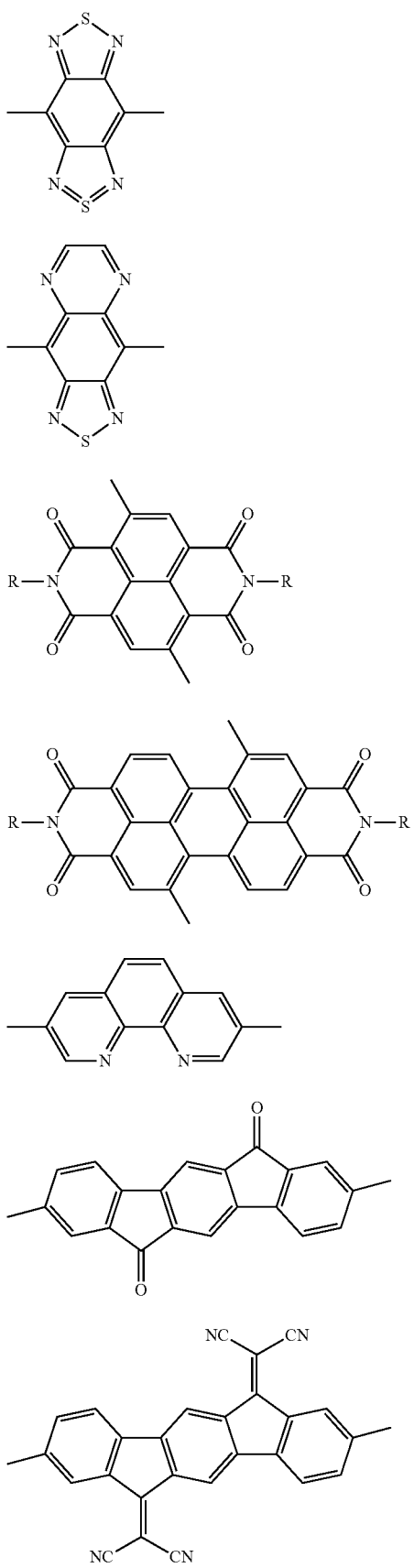

Although the above list for various A groups is provided, it is intended that in certain embodiments, each A may be independently chosen from any subset of the above list.

In certain embodiments any A may be A1. In certain embodiments, any A may be A2. In certain embodiments, any A may be A3. In certain embodiments, any A may be A4. In certain embodiments, any A may be A5. In certain embodiments, any A may be A6. In certain embodiments, any A may be A7. In certain embodiments, any A may be A8. In certain embodiments, any A may be A9. In certain embodiments, any A may be A10. In certain embodiments, any A may be A11. In certain embodiments, any A may be A12. In certain embodiments, any A may be A13. In certain embodiments, any A may be A14. In certain embodiments, any A may be A15. In certain embodiments, any A may be A16. In certain embodiments, any A may be A17. In certain embodiments, any A may be A18. In certain embodiments, any A may be A19. In certain embodiments, any A may be A20. In certain embodiments, any A may be A21. In certain embodiments, any A may be A22. In certain embodiments, any A may be A23. In certain embodiments, any A may be A24. In certain embodiments, any A may be A25. In certain embodiments, any A may be A26. In certain embodiments, any A may be A27. In certain embodiments, any A may be A28. In certain embodiments, any A may be A29. In certain embodiments, any A may be A30. In certain embodiments, any A may be A31.

In the A groups listed above, where applicable s is any integer from 1 to 4 when A is within the interior of the compound as opposed to a terminal group and is any integer from 1 to 5 when A is an end-cap (terminal) A group. In the above A groups when N is substituted with R, each R substituent may be, for example, independently H, alkyl, alkenyl or alkynyl, including straight or branched $C_{1-20}$ alkyl, straight or branched $C_{2-20}$ alkenyl, straight or branched $C_{2-20}$ alkynyl, straight or branched heteroalkyl having up to 20 backbone atoms in the main chain provided that the heteroatom is not bonded to N, alkaryl, alkheteroaryl, heteroalkaryl, heteroalkheteroaryl, aralkyl, arheteroalkyl, heteroaralkyl, heteroarheteroalkyl.

Although the above A groups have been depicted as divalent, when a particular A groups is an end-cap (or terminal) group, that group will be monovalent if unsubstituted. As well, although the above A groups are depicted as having backbone connections at particular positions, where possible the backbone connections may occur at other available positions provided that the aromatic nature of each group is maintained and that the conjugation between the each aromatic or heteroaromatic group along the chain is maintained.

Also, it will be appreciated that any of the above A groups may be substituted at any suitable position with one or more substituents that allows for the particular A group when substituted to maintain its overall electron withdrawing character. In various embodiments, such substituents may include electron donating substituents or electron withdrawing substituents.

In various embodiments, such substituents may include H, alkyl, alkenyl or alkynyl, including straight or branched $C_{1-20}$ alkyl, straight or branched $C_{2-20}$ alkenyl, straight or branched $C_{2-20}$ alkynyl, straight or branched heteroalkyl having up to 20 backbone atoms in the main chain provided that the heteroatom is not bonded to N, alkaryl, alkheteroaryl, heteroalkaryl, heteroalkheteroaryl, aralkyl, arheteroalkyl, heteroaralkyl, heteroarheteroalkyl.

As indicated, in certain embodiments each A group may be substituted with one or more electron withdrawing substituent or electron donating substituent, on any position that is available on any particular A group for such substitution, provided that when substituted the electronic character of each A is electron accepting.

An "electron withdrawing substituent" is a substituent that has a tendency to pull electrons away from the backbone of the aromatic or heteroaromatic group, on which it is substituted, towards the substituent, creating an electron-rich region at or near the substituent. Electron-withdrawing substituents include halo, fluoroalkyl (including perfluoroalkyl), carboxyl, cyano, ammonio, nitro, thionyl, sulfonyl, amido linked to the backbone through the oxygen, pyridinium, phosphonium, pyridyl, thiazolyl, oxadiazolyl and triazolyl groups.

Thus, in various embodiments, where applicable each A group may independently be substituted with one or more halo group, one or more fluoroalkyl group, one or more perfluoroalkyl group, one or more carboxyl group, one or more cyano group, one or more ammonio group, one or more nitro group, one or more thionyl group, one or more sulfonyl group, one or more amido group linked to the backbone through the oxygen, one or more pyridinium group, one or more phosphonium group, one or more pyridyl group, one or more thiazolyl group, one or more oxadiazolyl group or one or more triazolyl group, or any combination thereof.

An "electron donating substituent" is a substituent that is electron rich and thus has a tendency to push electrons toward the backbone of the aromatic or heteroaromatic group, on which it is substituted, into the conjugated system created by the backbones of the A and D groups as set out in formula I. Electron donating substituents include alkoxyl, alkylthio, amino, hydroxyl, amido connected to the backbone through the nitrogen, carboxyl connected to the backbone through the oxygen, phenyl, naphthyl, thienyl, furyl, pyrrolyl, carbazolyl, alkyl, alkenyl and alkynyl.

Thus, in various embodiments, where applicable each A group may independently be substituted with one or more alkoxyl group, one or more alkylthio group, one or more amino group, one or more hydroxyl group, one or more amido group connected to the backbone through the nitrogen, one or more carboxyl group connected to the backbone through the oxygen, one or more phenyl group, one or more naphthyl group, one or more thienyl group, one or more furyl group, one or more pyrrolyl group, one or more carbazolyl group, one or more alkyl group, one or more alkenyl group or one or more alkynyl group, or any combination thereof.

Each D in formula I is an independently selected an ethenylene group, an ethynylene group or a conjugated electron donating aromatic or heteroaromatic group having from 5 to 50 backbone atoms. Each D may be optionally substituted with one or more electron donating substituents or electron withdrawing substitutents provided that even when substituted the electronic character of each D is electron donating, as described above.

It will be appreciated that ethenylene groups, also commonly referred to as vinylene groups, will naturally have electron donating character. However, when adjacent to a strong electron withdrawing group, an ethenylene group may exhibit electron acceptor character. This phenomenon is described for example in Zhang et al., *Progress in Polymer Science* 31 (2006) pp. 893-948 and in Meier et al., *Tetrahedron Letters* 44 (2003) pp. 1915-1918. Thus, an ethenylene group may act as either electron donor or as electron acceptor, depending on which other groups are adjacent to the ethenylene group when included in the backbone of a larger molecule or polymer. In the presently described molecules according to formula I any ethenylene group is selected to function as a donor group and thus have electron donating character. Thus, when a given D group is selected as ethenylene and is adjacent to an A group (i.e. at the interface between an A block and a D block), the adjacent A group cannot be so strong as to influence the electronic character of the ethenylene group to make it an electron acceptor group. For example, the heteroaromatic 4,5-dicyanoimidazolyl group is a strong electron acceptor group. When conjugated directly to an ethenylene group, as in 2-vinyl-4,5-dicyanoimidazolyl(vinazene), both groups together act as acceptor groups, forming an A block. Thus, in the present molecules, any ethenylene group in the backbone cannot be adjacent to a 4,5-dicyanoimidazolyl group.

In certain embodiments, each D is independently ethenylene, ethynylene or one of the following groups, any of which may be further substituted where appropriate:

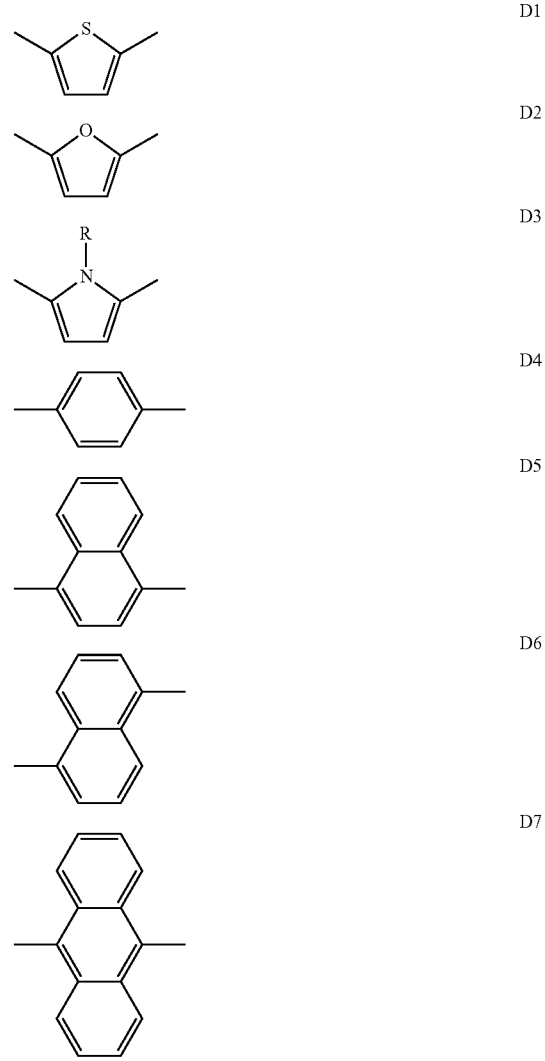

-continued

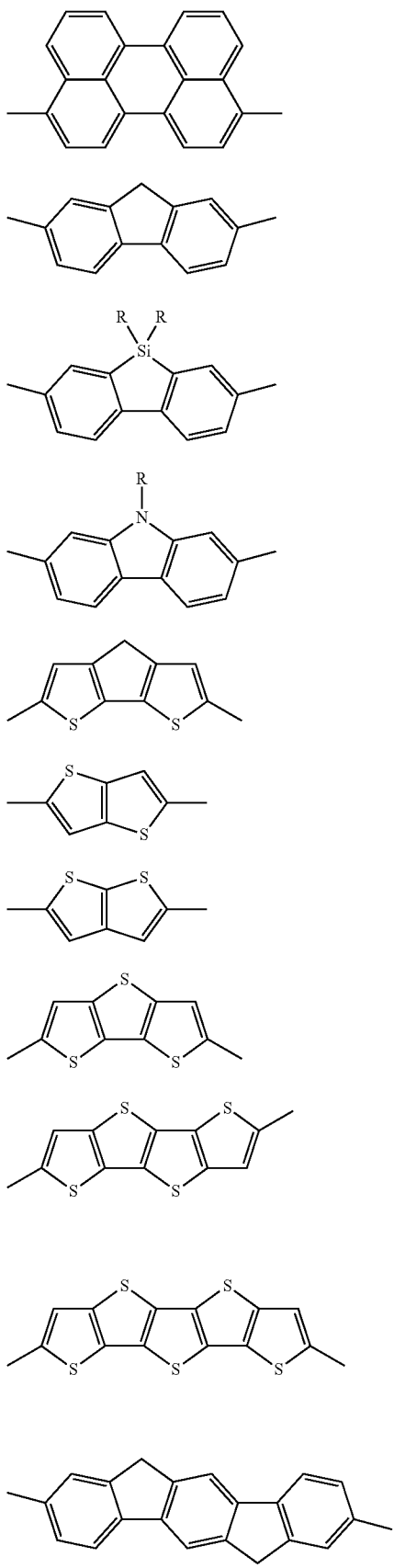

D8
D9
D10
D11
D12
D13
D14
D15
D16
D17
D18

-continued

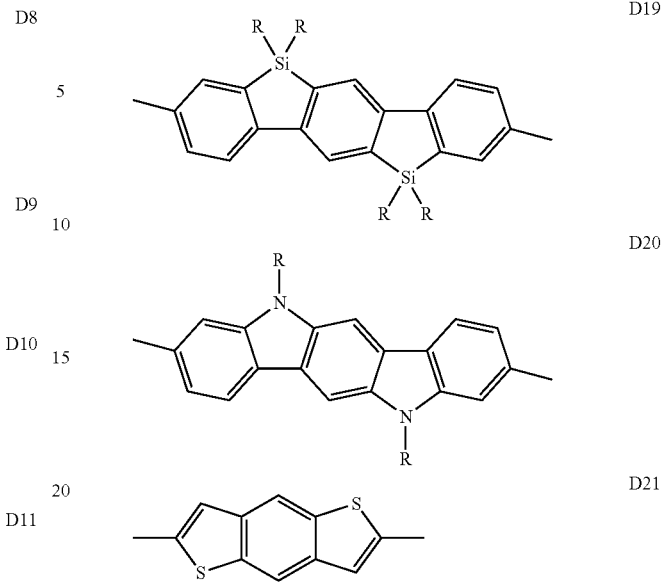

D19
D20
D21

Although the above list for various D groups is provided, it is intended that in some embodiments, each D may be independently chosen from any subset of the above list.

In certain embodiments any D may be D1. In certain embodiments, any D may be D2. In certain embodiments, any D may be D3. In certain embodiments, any D may be D4. In certain embodiments, any D may be D5. In certain embodiments, any D may be D6. In certain embodiments, any D may be D7. In certain embodiments, any D may be D8. In certain embodiments, any D may be D9. In certain embodiments, any D may be D10. In certain embodiments, any D may be D11. In certain embodiments, any D may be D12. In certain embodiments, any D may be D13. In certain embodiments, any D may be D14. In certain embodiments, any D may be D15. In certain embodiments, any D may be D16. In certain embodiments, any D may be D17. In certain embodiments, any D may be D18. In certain embodiments, any D may be D19. In certain embodiments, any D may be D20. In certain embodiments, any D may be D21.

In the D groups listed above, when N or Si is substituted with R, each R substituent may be, for example, independently H, alkyl, alkenyl or alkynyl, including straight or branched $C_{1-20}$ alkyl, straight or branched $C_{2-20}$ alkenyl, straight or branched $C_{2-20}$ alkynyl, straight or branched heteroalkyl having up to 20 backbone atoms in the main chain provided that the heteroatom is not bonded to N or Si, alkaryl, alkheteroaryl, heteroalkaryl, heteroalkheteroaryl, aralkyl, arheteroalkyl, heteroaralkyl, heteroarheteroalkyl.

Although the above D groups are depicted as having backbone connections at particular positions, where possible the backbone connections may occur at other available positions provided that the aromatic nature of each group is maintained and that the conjugation between the each aromatic or heteroaromatic group along the chain is maintained.

Also, it will be appreciated that any of the above D groups may be substituted at any suitable position with one or more substituents that allows for the particular D group when substituted maintaining its overall electron donating character. In various embodiments, such substituents may include electron donating substituents or electron withdrawing substituents.

In various embodiments, such substituents may include H, alkyl, alkenyl or alkynyl, including straight or branched $C_{1-20}$ alkyl, straight or branched $C_{2-20}$ alkenyl, straight or branched $C_{2-20}$ alkynyl, straight or branched heteroalkyl having up to 20 backbone atoms in the main chain provided that the heteroatom is not bonded to N, alkaryl, alkheteroaryl, heteroalkaryl, heteroalkheteroaryl, aralkyl, arheteroalkyl, heteroaralkyl, heteroarheteroalkyl.

As indicated, in certain embodiments each D group may be substituted with one or more electron donating substituent or electron withdrawing substituent, on any position that is available on any particular D group for such substitution.

Thus, in various embodiments, where applicable each D group may independently be substituted with one or more alkoxyl group, one or more alkylthio group, one or more amino group, one or more hydroxyl group, one or more amido group connected to the backbone through the nitrogen, one or more carboxyl group connected to the backbone through the oxygen, one or more phenyl group, one or more naphthyl group, one or more thienyl group, one or more furyl group, one or more pyrrolyl group, one or more carbazolyl group, one or more alkyl group, one or more alkenyl group or one or more alkynyl group, or any combination thereof.

In various embodiments, where applicable each D group may independently be substituted with one or more halo group, one or more fluoroalkyl group, one or more perfluoroalkyl group, one or more carboxyl group, one or more cyano group, one or more ammonio group, one or more nitro group, one or more thionyl group, one or more sulfonyl group, one or more amido group linked to the backbone through the oxygen, one or more pyridinium group, one or more phosphonium group, one or more pyridyl group, one or more thiazolyl group, one or more oxadiazolyl group or one or more triazolyl group, or any combination thereof, provided that even when substituted the electronic character of each D is electron donating, as described above.

Each n in formula I is independently an integer from 1 to 20. Each p in formula I is independently an integer from 1 to 10. It will be appreciated that, depending on the particular group chosen for each A group and each D group, the value for n for a given A block and the value of p for a given D block will vary. The number of A groups in each A block and the number of D groups in each D block should be chosen so that the compound has an overall acceptor character (n-type character). In certain embodiments, the total number of D groups from all D blocks is less than the total number of A groups from all A blocks. In some embodiments, each n is chosen to be greater than or equal to each p.

r in formula I is an integer having a value of 2 or greater, or in some embodiments from 2 to 20.

In particular embodiments, the compound of formula I is N-1, N-2, N-3, N-4, N-5, N-6, N-7, N-8, N-9, N-10 or N-11, as shown below.

N-1

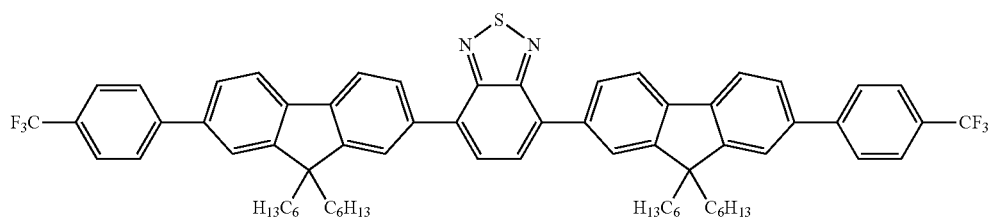

N-2

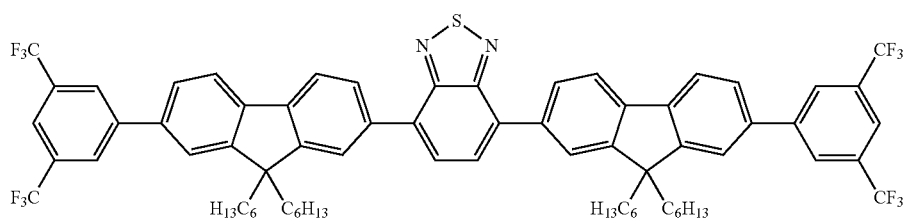

N-3

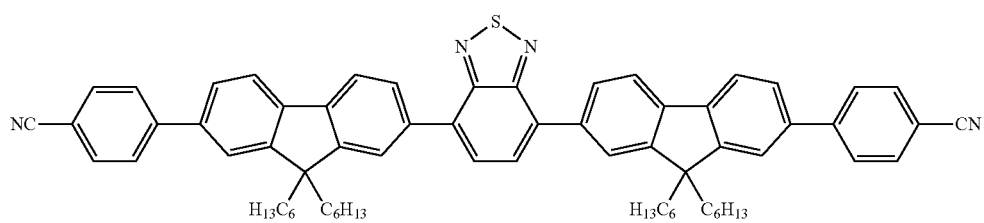

N-4

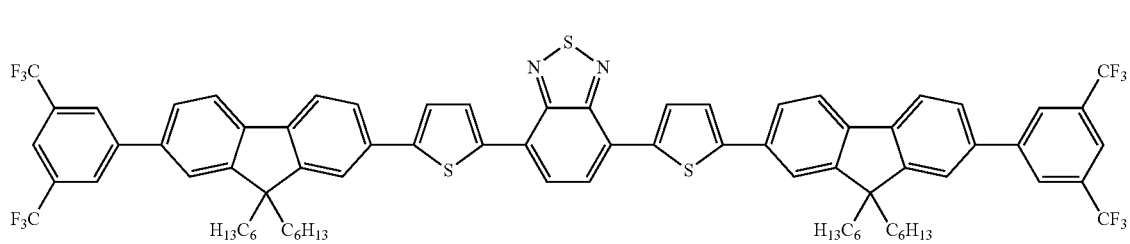

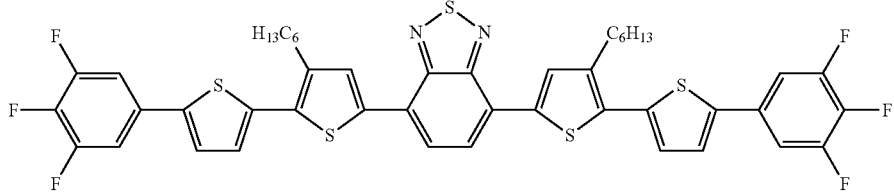

N-5

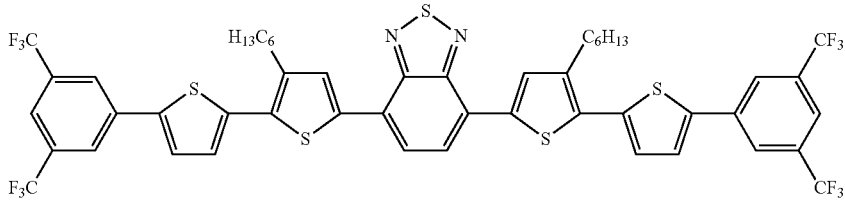

N-6

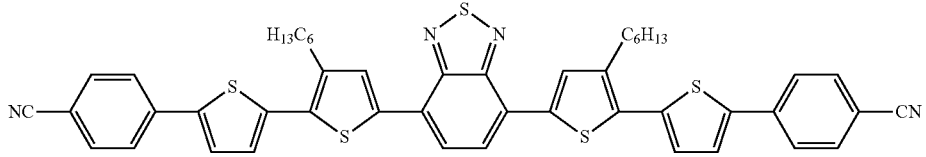

N-7

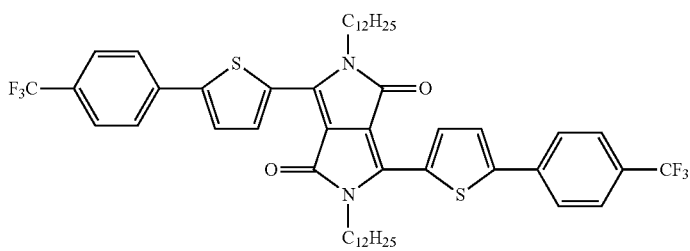

N-8

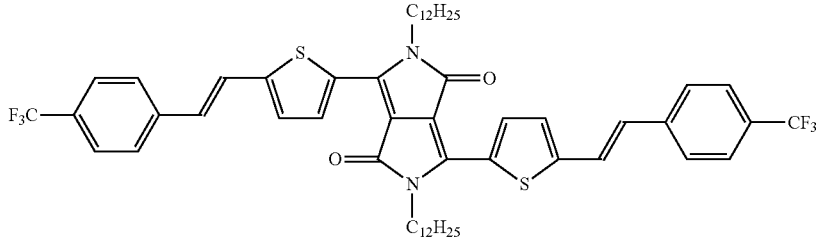

N-9

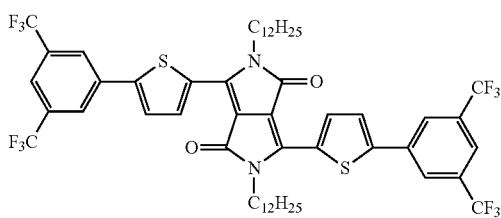

N-10

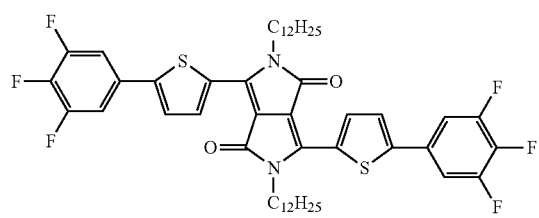

N-11

In one embodiment, the compound of formula I is N-1. In another embodiment, the compound of formula I is N-2. In another embodiment, the compound of formula I is N-3. In another embodiment, the compound of formula I is N-4. In another embodiment, the compound of formula I is N-5. In another embodiment, the compound of formula I is N-6. In another embodiment, the compound of formula I is N-7. In another embodiment, the compound of formula I is N-8. In another embodiment, the compound of formula I is N-9. In another embodiment, the compound of formula I is N-10. In another embodiment, the compound of formula I is N-11.

The compounds of formula I can be synthesized using commercially available reagents, using routine chemical techniques, including via the Suzuki coupling reaction, the Stille coupling reaction, the Heck coupling reaction, the Wittig-Horner reaction, the Knoevenagel condensation reaction or the Sonogashira reaction.

Particular reaction schemes to synthesize compounds N-1 to N-11 are set out in the Examples below, in Schemes 1 to 4, which reaction schemes may be adapted for synthesis of other compounds within formula I.

The compounds of formula I may exhibit high solubility and may be easily purified using standard techniques including column chromatography and/or recrystallization methods. Thus, the compounds of formula I may be synthesized to high purity.

The alternating system of conjugated acceptor blocks and donor blocks with acceptor blocks at either end of the compounds of formula I provides n-type compounds that can exhibit strong absorption in the visible range, for example in the 410-610 nm range. Thus, compounds of formula I can possess photophysical properties that may make them suitable as electron acceptor materials in organic electronic devices, including organic photovoltaic cells.

The energy level of the HOMO (highest occupied molecular orbital) and the LUMO (lowest unoccupied molecular orbital) of compounds of formula I can be tuned through selection of the specific electron donating D groups and electron withdrawing A groups included in a particular compound, along with the number and length of each acceptor block and donor block. Thus, the bandgap (the difference in energy level between the HOMO and the LUMO) and the absorption range for compounds of formula I can be varied by varying the A and D groups used in the compounds, based on considerations such as the particular energy levels of the donor material used in an electronic device in which the compounds of formula I are to be used as acceptor material.

The tunability of the compounds, along with the ease in synthesis and purification, can make the compounds of formula I useful for general application as acceptor n-type material. For example, the compounds of formula I may be used as light harvesting and electron transporting materials in organic photovoltaic (OPV) cells or as emissive and/or electron transporting material in OLEDs.

The compounds of formula I are suitable for solution processing, thus allowing for production of a thin film containing such a compound, for inclusion in an organic electronic device. Thus, there is presently provided a thin film comprising a compound of formula I.

The thin film is a layer comprising a compound of formula I as described above, which may be formed to be in the order of from about 0.1 to about 1000 nm thick, from about 1 to about 500 nm thick, from about 5 to about 250 nm thick, or from about 5 to about 100 nm thick.

When used in a solar cell, the thin film may constitute the photoactive layer of the solar cell, and thus may further comprise a suitable p-type electron donor material.

For example, the donor material may comprise one or more of regioregular poly(3-hexylthiophene-2,5-diyl) (P3HT), regioregular poly(3-ocylthiophene-2,5-diyl) (P3OT), regioregular poly(quarterthiophene) (PQT), a-poly(phenylene ethynylene)-poly(phenylene vinylene) (A-PPE-PPV), poly [2-methoxy-5-(2'-ethyl-hexyloxy)-1,4-phenylene vinylene] (MEH-PPV), and poly[2-methoxy-5-(3,7-dimethyloctyloxy)-1,4-phenylenevinylene] (MDMO-PPV), poly(9,9-dihexyl-fluoren-2,7-diyl-alt-bithiophen-2,5'-diyl), poly(N-alkyl-carbazo-2,7-diyl-alt-4,7-dithienyl-2,1,3-benzothiadiazo-2,5''-diyl), poly[2,6-(4,4-bis(2-ethylhexyl)-4H-cyclopenta[2,1-b:3,4-b']dithiophene)-alt-4,7-(2,1,3-benzothiadiazole)] (PCPDTBT), poly(9,9-dioctyl-silafluoren-2,7-diyl-alt-4,7-dithienyl-2,1,3-benzothiadiazo-2,5''-diyl), poly[2,6-(4,4-bis(2-ethylhexyl)-4H-cyclopenta[2,1-b:3,4-b']dithiophenesilole)-alt-4,7-(2,1,3-benzothiadiazole)]. In a particular embodiment, the donor material comprises P3HT. In one embodiment, the donor material is P3HT.

The thin film may be formed on a suitable substrate, which may be any solid substrate, including indium tin oxide (ITO) coated glass or plastic, fluorine tin oxide (FTO) coated glass or plastic, quartz, glass, mica, a plastic substrate such as polyethylene terephthalate or polycarbonate, paper, metal, or silicon. The thin film may also be layered onto another layer when forming a multilayered device, or onto an electrode.

To form the thin film, the compound of formula (I) and any additional film components may be dissolved in a suitable organic solvent. Suitable solvents include chloroform, toluene, a xylene, ethyl benzoate, methyl benzoate, 1,1,2,2-tetrachloroethane, THF, dioxane, chlorobenzene, dichlorobenzenes, mesitylene and mixtures of the aforesaid solvents.

The thin film may be formed on a suitable surface using standard deposition or coating methods including solution coating. Solution coating includes spin coating, casting, microgravure coating, gravure coating, bar coating, roll coating, wire bar coating, dip coating, spray coating, screen printing, flexo printing, offset printing and inkjet printing.

The compounds of formula (I) and thin films containing such compounds may be used to construct solar cells. The compounds of formula (I) and thin films containing such compounds may form the electron acceptor in the photoactive layer in an organic photovoltaic cell. Such devices and layers are known in the art.

Thus, there is presently provided a device comprising a compound of formula (I) or a thin film comprising a compound of formula (I).

Figure 4:
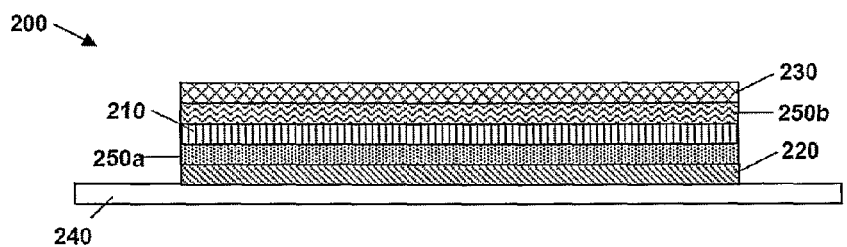
FIG. 4 is a representation of an electronic device incorporating a compound of formula I as an electron acceptor material.

In one embodiment, with reference to FIG. 4, device 200 comprises a photoactive layer 210 comprising a compound of formula (I) as an electron acceptor. The photoactive layer 210 further includes an electron donor, as described above.

Active layer 210 is disposed between cathode 220 and anode 230. In certain embodiments, photoactive layer 210 is from about 5 to about 100 nm thick.

The anode 230 is any material capable of conducting holes and injecting them into organic layers. Anode 230 may be gold, silver, fluorine tin oxide (FTO) or indium tin oxide (ITO), or conductive polymer layers. The anode 230 may be reflective, transparent, semi-transparent or translucent. In certain embodiments, the anode is transparent material such as ITO.

Cathode 220 is any material capable of conducting electrodes and injecting them into organic layers. Cathode 220 may be a low work function metal or metal alloy, including, for example, barium, calcium, magnesium, indium, aluminum, ytterbium, silver, a calcium: silver alloy, an aluminum: lithium alloy, or a magnesium:silver alloy, such as, for example an alloy wherein the atomic ratio of magnesium to silver is about 10:1 (U.S. Pat. No. 6,791,129) or an alloy where the atomic ratio of lithium to aluminum is about 0.1: 100 to about 0.3:100 (Kim et al. (2002) Curr. Appl. Phys. 2(4):335-338; Cha et al (2004) Synth. Met. 143(1): 97; Kim et al (2004) Synth. Met. 145(2-3): 229). The cathode 230 may be a single layer or have a compound structure. Cathode 230 may comprise layers of lithium fluoride, aluminium and silver. The cathode 230 may be reflective, transparent, semi-transparent or translucent.

In certain embodiments, one or more of the anode and the cathode may be deposited on a support 240, which may be transparent, semi-transparent or translucent. Support 240 may be rigid, for example quartz or glass, or may be a flexible polymeric substrate. Examples of flexible transparent semi-transparent or translucent substrates include, but are not limited to, polyimides, polytetrafluoroethylenes, polyethylene terephthalates, polyolefins such as polypropylene and polyethylene, polyamides, polyacrylonitrile and polyacrionitrile, polymethacrylonitrile, polystyrenes, polyvinyl chloride, and fluorinated polymers such as polytetrafluoroethylene.

The device may optionally comprise an additional layer such as a smoothing layer 250 between the photoactive layer 210 and the anode 220 (250*a*), the cathode 230 (250*b*) or both. The smoothing layer 250 may be a poly(ethylene dioxytiophene)/polystyrene sulfonic acid (PEDOT:PSS) layer or Ca. The smoothing layer may be from about 20 nm to about 50 nm.

In a particular embodiment, device 200 comprises the following layers: glass/ITO/PEDOT:PSS/active layer/Ca/Ag, in which the photoactive layer is formed from a ratio of P3HT: compound of formula I ranging from 1:1 to 1:4 weight ratio of P3HT:compound of formula I in chloroform. In particular embodiments, the weight ratio of P3HT:compound of formula I is 1:2 or 1:3.

In certain embodiments, the photoactive layer comprises a 1:2 weight ratio of P3HT:N-1. In certain other embodiments, the photoactive layer comprises a 1:2 weight ratio of P3HT: N-2. In certain other embodiments, the photoactive layer comprises a 1:2 weight ratio of P3HT:N-3. In certain other embodiments, the photoactive layer comprises a 1:2 weight ratio of P3HT:N-4. In certain other embodiments, the photoactive layer comprises a 1:2 weight ratio of P3HT:N-5. In certain other embodiments, the photoactive layer comprises a 1:2 weight ratio of P3HT:N-6. In certain other embodiments, the photoactive layer comprises a 1:2 weight ratio of P3HT: N-7. In certain other embodiments, the photoactive layer comprises a 1:2 weight ratio of P3HT:N-8. In certain other embodiments, the photoactive layer comprises a 1:2 weight ratio of P3HT:N-9. In certain other embodiments, the photoactive layer comprises a 1:2 weight ratio of P3HT:N-10. In certain other embodiments, the photoactive layer comprises a 1:2 weight ratio of P3HT:N-11. In certain other embodiments, the photoactive layer consists of a 1:2 weight ratio of P3HT:N-1. In certain other embodiments, the photoactive layer consists of a 1:2 weight ratio of P3HT:N-2. In certain other embodiments, the photoactive layer consists of a 1:2 weight ratio of P3HT:N-3. In certain other embodiments, the photoactive layer consists of a 1:2 weight ratio of P3HT:N-4. In certain other embodiments, the photoactive layer consists of a 1:2 weight ratio of P3HT:N-5. In certain other embodiments, the photoactive layer consists of a 1:2 weight ratio of P3HT:N-6. In certain other embodiments, the photoactive layer consists of a 1:2 weight ratio of P3HT:N-7. In certain other embodiments, the photoactive layer consists of a 1:2 weight ratio of P3HT:N-8. In certain other embodiments, the photoactive layer consists of a 1:2 weight ratio of P3HT:N-9. In certain other embodiments, the photoactive layer consists of a 1:2 weight ratio of P3HT:N-10. In certain other embodiments, the photoactive layer consists of a 1:2 weight ratio of P3HT:N-11.

The above-mentioned devices may be prepared by layering the relevant layers on top of one another. The layers may be prepared by methods known in the art, including solution coating techniques mentioned above. Solution coating steps may be carried out in an inert atmosphere, such as, for example, under nitrogen gas. Alternatively, layers may be prepared by thermal evaporation or by vacuum deposition. Metallic layers may be prepared by known techniques, such as, for example, thermal or electron-beam evaporation, chemical-vapour deposition or sputtering.

The solar cells have been described above with a thin film comprising the electron donor material and electron acceptor material. However, it will be appreciated that the present compounds can be used to form devices in which the n-type electron acceptor material is in a separate layer from the p-type electron donor material.

The solar cell devices described herein may be used in stacked solar cells, in which two or more solar cells are stacked in a single device, for example as described in published patent application US 20070090371.

The following examples are intended as exemplary only and are not in any way intended to limit the scope of the present invention.

EXAMPLES

Instruments.
$^1$H and $^{13}$C NMR data were performed on a Bruker DPX 400 MHz spectrometer with chemical shifts referenced to CDCl$_3$. Matrix assisted laser desorption/ionization time-of-flight (MALDI-TOF) mass spectra were obtained on a Bruker Autoflex TOF/TOF instrument using dithranol as a matrix and silver trifluoroacetate as an ionizing salt when necessary. Differential scanning calorimetry (DSC) was carried out under nitrogen on a DSC Q100 instrument (scanning rate of 10° C.·min$^{-1}$). Thermal gravimetric analysis (TGA) was carried out using TGA Q500 instrument (heating rate of 10° C.·min$^{-1}$). Cyclic voltammetry experiments were performed using an Autolab potentiostat (model PGSTAT30) by Echochimie. All CV measurements were recorded in dichloromethane with 0.1 M tetrabutylammonium hexafluorophosphate as supporting electrolyte (scan rate of 100 mV·s$^{-1}$). The experiments were performed at room temperature with a conventional three electrode configuration consisting of a platinum wire working electrode, a gold counter electrode, and a Ag/AgCl in 3 M KCl reference electrode. The measured potentials were converted to SCE (saturated calomel electrode) and the corresponding ionization potential (IP) and electron affinity (EA) values were derived from the onset redox potentials, based on −4.4 eV as the SCE energy level relative to vacuum (EA=E$_{red\text{-}onset}$+4.4 eV, IP=E$_{ox\text{-}onset}$+4.4 eV). UV-Vis spectra were recorded on a Shimadzu model 2501-PC UV-VIS spectrometer, and photoluminescence (PL) spectra were measured on a Perkin-Elmer (LS50B) spectrofluorimeter.

Example 1

Synthesis of N-1, N-2, N-3 According to Scheme 1

Scheme 1

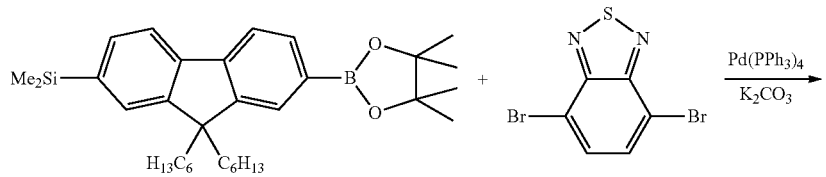

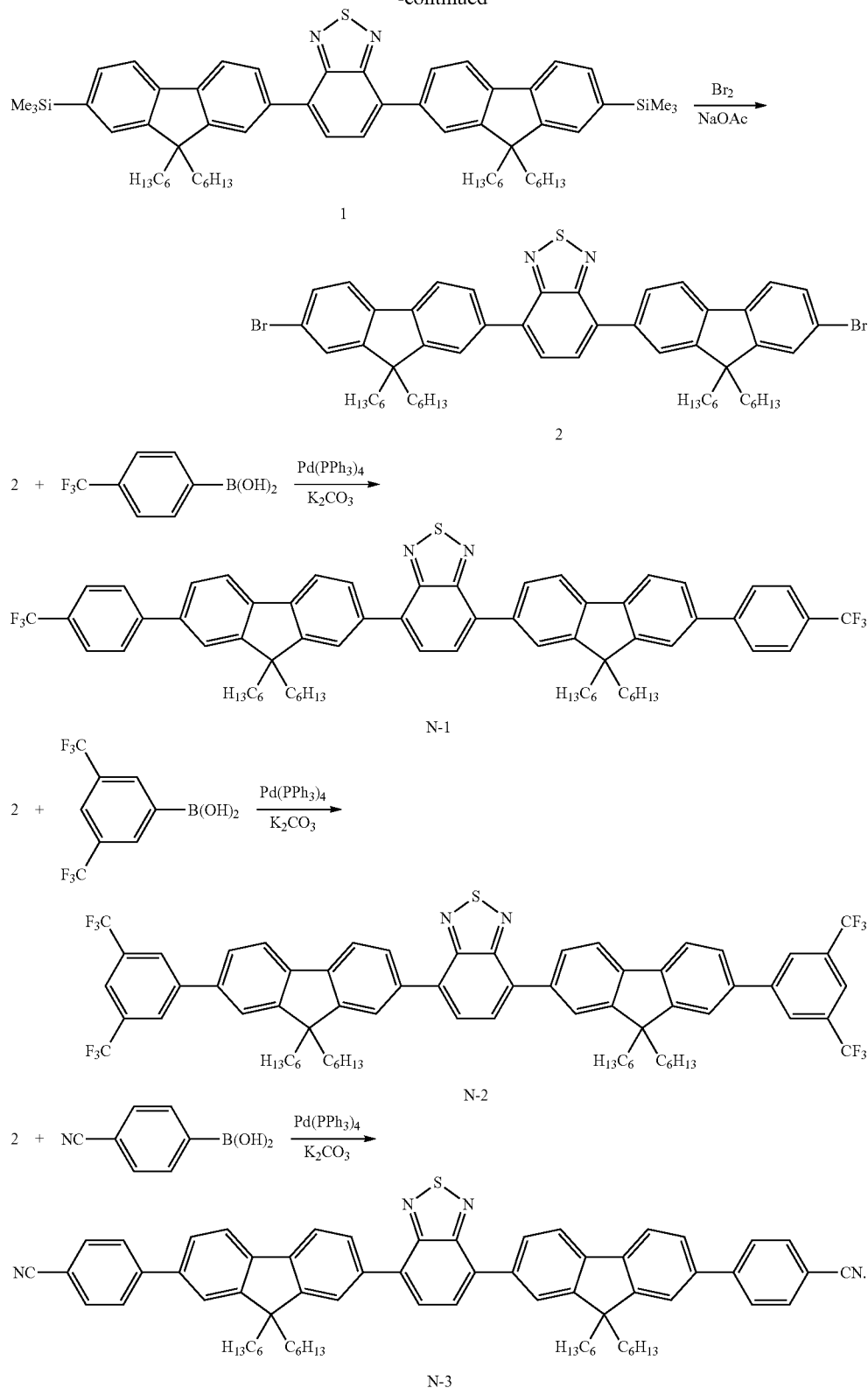
Synthesis of 1
4,7-Dibromo-2,1,3-benzothiadiazole (0.44 g, 1.5 mmol) and 7-Trimethylsilyl-9,9-di-n-hexylfluorene-2-boronate (1.80 g, 3.4 mmol) were dissolved in toluene (15 mL) and an aqueous solution of 2M $K_2CO_3$ (4.5 mL) was added. The mixture was purged with nitrogen for 30 min and tetrakis (triphenylphosphine)palladium (0.070 g, 0.06 mmol) was added. The reaction mixture was heated at 90° C. for 24 h. The cooled mixture was poured into brine and extracted several times with diethyl ether. The combined extracts were dried over MgSO$_4$ and filtered. The filtrate was dried under vacuum and the residue chromatographed on silica gel with 1% ethyl acetate in hexane. The product was then recrystallised from ethanol/hexane to give bright yellow crystals (1.26 g, 89% yield). $^1$H NMR (CDCl$_3$): δ 8.02 (d, 1H, J=7.6 Hz), 7.97 (s, 1H), 7.89 (overlapping s, 1H), 7.88 (overlapping d, 1H, J=8.4 Hz), 7.76 (d, 1H, J=7.2 Hz), 7.53 (overlapping d, 1H, J=8.0 Hz), 7.52 (overlapping s, 1H), 2.04 (m, 4H), 1.13 (m, 12H), 0.82 (overlapping m, 4H) 0.78 (overlapping t, 6H, J=7.2 Hz), 0.34 (s, 9H). $^{13}$C NMR (CDCl$_3$): δ 154.58, 151.51, 150.69, 141.47, 139.53, 136.50, 133.82, 132.06, 128.28, 128.06, 127.86, 124.21, 119.99, 119.39, 55.34, 40.26, 31.56, 29.81, 24.00, 22.66, 14.15, −0.70. Anal. Calcd for C$_{62}$H$_{84}$N$_2$Si$_2$S$_3$: C, 78.75; H, 8.95; N, 2.96; S, 3.39. Found: C, 78.28; H, 9.01; N, 2.97; S, 3.58. MS (MALDI-TOF) m/z 944.55 (M); calcd. for C$_{62}$H$_{84}$N$_2$Si$_2$S$_3$=944.59.

Synthesis of 2

A THF solution (20 mL) containing 1 (0.94 g, 1.0 mmol) and anhydrous sodium acetate (0.16 g, 2.0 mmol) was cooled to 0° C. Bromine (0.64 g, 4.0 mmol) was added and the mixture stirred for 45 min in the dark. The reaction was quenched by addition of triethylamine (1.12 mL, 8.0 mmol), followed by an excess of aqueous Na$_2$SO$_4$. The product was extracted into diethyl ether, and the extract washed with aqueous Na$_2$SO$_4$ and dried over MgSO$_4$. After filtration, the filtrate was evacuated dry and the residue recrystallised from hot hexane to give the product as yellow solids (0.91 g, 94% yield). $^1$H NMR (CDCl$_3$): δ 8.01 (d, 1H, J=7.6 Hz), 7.95 (s, 1H), 7.88 (s, 1H), 7.83 (d, 1H, J=8.0 Hz), 7.63 (d, 1H, J=8.0 Hz), 7.51 (overlapping s, 1H), 7.50 (overlapping d, 1H, J=9.6 Hz), 2.08-1.94 (m, 4H), 1.10 (m, 12H), 0.78 (overlapping m and t (J=7.2 Hz), 10H). $^{13}$C NMR (CDCl$_3$): δ 154.50, 153.75, 150.94, 140.44, 139.87, 136.80, 133.74, 130.26, 128.51, 128.07, 126.48, 124.18, 121.46, 119.99, 55.77, 40.38, 31.64, 29.84, 24.00, 22.73, 14.15. Anal. Calcd for C$_{56}$H$_{66}$N$_2$Br$_2$S: C, 70.13; H, 6.94; N, 2.92; S, 3.34. Found: C, 69.93; H, 6.94; N, 3.06; S, 3.51. MS (MALDI-TOF) m/z 958.20 (M); calcd. for C$_{56}$H$_{66}$N$_2$Br$_2$S=958.33.

Synthesis of N-1

Reaction system: 2 (0.29 g, 0.30 mmol), 4-trifluoromethylphenylboronic acid (0.17 g, 0.90 mmol), Pd(PPh$_3$)$_4$ (0.014 g, 0.012 mmol). The product was recrystallised from hexane to give bright yellow solids (0.29 g, 88% yield). $^1$H NMR (CDCl$_3$): δ 8.06 (d, 1H, J=8.0 Hz), 8.00 (s, 1H), 7.92 (t, 2H, J=3.6 Hz), 7.87 (d, 1H, J=8.0 Hz), 7.79 (d, 2H, J=8.0 Hz), 7.74 (d, 2H, J=8.4 Hz), 7.63 (d, 1H, J=8.0 Hz), 7.61 (s, 1H), 2.09 (m, 4H), 1.11 (m, 12H), 0.83 (m, 4H), 0.77 (t, 6H, J=6.8 Hz). $^{13}$C NMR (CDCl$_3$): δ 154.57, 152.47, 151.64, 145.39, 141.09, 140.85, 138.98, 136.75, 133.80, 128.51, 128.11, 127.64, 126.53, 125.91, 124.25, 121.91, 120.59, 120.18, 55.64, 40.49, 31.65, 29.89, 24.11, 22.73, 14.14. Anal. Calcd for C$_{70}$H$_{74}$N$_2$F$_6$S$_3$: C, 77.17; H, 6.85; N, 2.57; S, 2.94. Found: C, 76.93; H, 7.26; N, 2.58; S, 3.05. MS (MALDI-TOF) m/z 1088.51 (M); calcd. for C$_{70}$H$_{74}$N$_2$F$_6$S$_3$=1088.55.

Synthesis of N-2

Reaction system: 2 (0.29 g, 0.30 mmol), 3,5-bis(trifluoromethyl)benzeneboronic acid (0.23 g, 0.90 mmol), Pd(PPh$_3$)$_4$ (0.014 g, 0.012 mmol). The product was recrystallised from ethanol/hexane to give yellow crystals (0.36 g, 97% yield). $^1$H NMR (CDCl$_3$): δ 8.09 (overlapping s, 2H), 8.07 (overlapping d, 1H, J=8.4 Hz), 8.02 (s, 1H), 7.93 (t, 2H, J=8.0 Hz), 7.88 (s, 2H), 7.63 (d, 1H, J=7.6 Hz), 7.59 (s, 1H), 2.12 (m, 4H), 1.12 (m 12H), 0.82 (overlapping m, 4H), 0.78 (t, 6H, 6.8 Hz). $^{13}$C NMR (CDCl$_3$): δ 154.55, 152.85, 151.66, 144.01, 141.79, 140.54, 137.42, 137.03, 133.79, 132.50, 132.17, 128.58, 128.14, 127.41, 126.62, 125.01, 124.31, 122.30, 121.75, 120.86, 120.36, 55.79, 40.43, 31.63, 29.82, 24.09, 22.71, 14.12. Anal. Calcd for C$_{72}$H$_{72}$N$_2$F$_{12}$S$_3$: C, 70.57; H, 5.92; N, 2.29; S, 2.62. Found: C, 68.18; H, 6.50; N, 2.24; S, 2.48. MS (MALDI-TOF) m/z 1224.65 (M); calcd. for C$_{72}$H$_{72}$N$_2$F$_{12}$S$_3$=1224.52.

Synthesis of N-3

Reaction system: 2 (0.29 g, 0.30 mmol), 4-cyanophenylboronic acid (0.13 g, 0.90 mmol), Pd(PPh$_3$)$_4$ (0.014 g, 0.012 mmol). The product was purified on silica gel column chromatography with 1-5% ethyl acetate in hexane as eluent. The product was then recrystallised from hexane/THF to give yellow needles (0.19 g, 63% yield). $^1$H NMR (CDCl$_3$): δ 8.06 (d, 1H, J=8.0 Hz), 8.01 (s, 1H), 7.92 (overlapping s and d (J=7.6 Hz), 2H), 7.87 (d, 1H, J=8.0 Hz), 7.81-7.76 (m, 4H), 7.62 (d, 1H, J=8.0 Hz), 7.60 (s, 1H), 2.10 (m, 4H), 1.11 (m; 12H), 0.82 (overlapping m, 4H), 0.77 (overlapping t, 6H, J=7.2 Hz). $^{13}$C NMR (CDCl$_3$): δ 154.54, 152.60, 151.67, 146.30, 141.58, 140.65, 138.33, 136.92, 133.77, 132.77, 128.55, 128.11, 127.93, 126.55, 124.27, 121.79, 120.71, 120.28, 119.18, 110.88, 55.68, 40.46, 31.63, 29.86, 24.09, 22.71, 14.13. Anal. Calcd for C$_{70}$H$_{74}$N$_4$S: C, 83.79; H, 7.43; N, 5.58; S, 3.20. Found: C, 83.33; H, 7.54; N, 5.62; S, 3.21.

Example 2

Synthesis of N-4 According to Scheme 2

Scheme 2

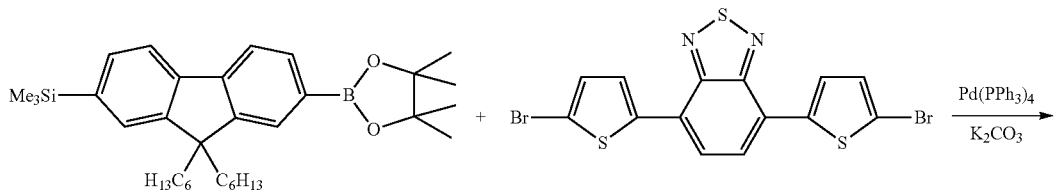

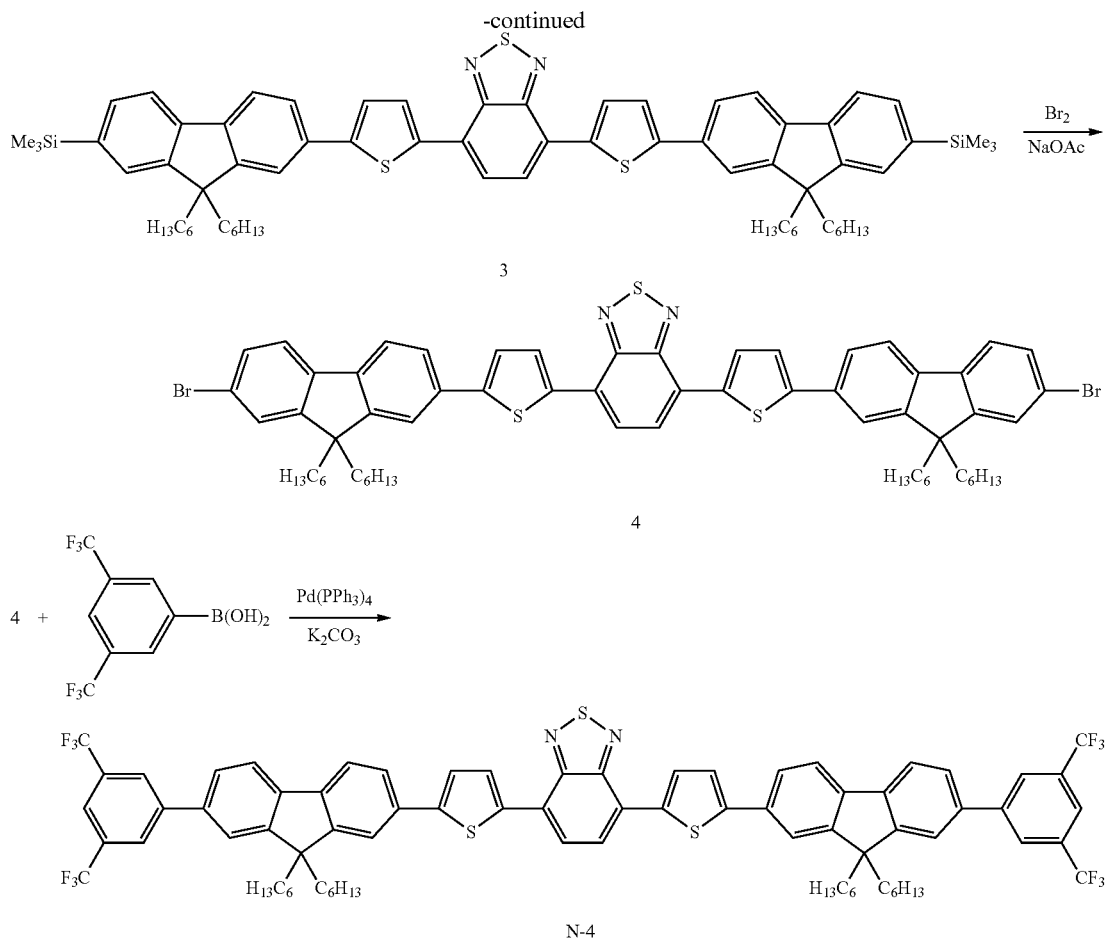

Synthesis of 3

4,7-bis(5-bromo-2-thienyl)-2,1,3-benzothiadiazole (0.69 g, 1.5 mmol) and 7-Trimethylsilyl-9,9-di-n-hexylfluorene-2-boronate (1.80 g, 3.4 mmol) were dissolved in toluene (15 mL) and an aqueous solution of 2 M $K_2CO_3$ (4.5 mL) was added. The mixture was purged with nitrogen for 30 min and tetrakis(triphenylphosphine)palladium (0.070 g, 0.06 mmol) was added. The reaction mixture was heated at 90° C. for 24 h. The cooled mixture was poured into brine and extracted several times with diethyl ether. The combined extracts were dried over $MgSO_4$ and filtered. The filtrate was dried under vacuum and the residue chromatographed on silica gel with 0-2% ethyl acetate in hexane. The product was then recrystallised from ethanol/hexane to give red solids (1.36 g, 82% yield). $^1$H NMR ($CDCl_3$): δ 8.16 (d, 1H, J=4.0 Hz), 7.94 (s, 1H), 7.75-7.67 (m, 4H), 7.52-7.49 (m, 3H), 2.03 (t, 4H, J=8.4 Hz), 1.15-1.09 (unresolved m, 12H), 0.77 (t, 6H, J=6.4 Hz), 0.72-0.67 (unresolved m, 4H), 0.33 (s, 9H). $^{13}$C NMR ($CDCl_3$): δ 152.86, 152.02, 150.29, 146.73, 141.35, 139.52, 138.52, 133.20, 132.06, 128.86, 127.77, 126.02, 125.49, 124.95, 124.09, 120.34, 119.20, 55.34, 40.35, 31.52, 29.73, 23.86, 22.64, 14.13, 0.72. Anal. Calcd for $C_{70}H_{88}N_2S_3Si_2$: C, 75.75; H, 7.99; N, 2.52; S, 8.67. Found: C, 75.44; H, 8.10; N, 2.65; S, 8.84. MS (MALDI-TOF) m/z 1108.72 (M); calcd. for $C_{70}H_{88}N_2S_3Si_2$=1108.56.

Synthesis of 4

A THF solution (20 mL) containing 3 (1.11 g, 1.0 mmol) and anhydrous sodium acetate (0.16 g, 2.0 mmol) was cooled to 0° C. Bromine (0.64 g, 4.0 mmol) was added and the mixture stirred for 45 min in the dark. The reaction was quenched by addition of triethylamine (1.12 mL, 8.0 mmol), followed by an excess of aqueous $Na_2SO_4$. The product was extracted into diethyl ether, and the extract washed with aqueous $Na_2SO_4$ and dried over $MgSO_4$. After filtration, the filtrate was evacuated dry and the residue recrystallised from hot hexane to give red solids (1.06 g, 94% yield). $^1$H NMR ($CDCl_3$): δ 8.15 (d, 1H, J=3.6 Hz), 7.94 (s, 1H), 7.72-7.67 (m, 2H), 7.64 (s, 1H), 7.57 (d, 1H, J=8.4 Hz), 7.52-7.47 (m, 3H), 2.07-1.94 (m, 4H), 1.18-1.08 (unresolved in, 12H), 0.78 (t, 6H, J=6.8 Hz), 0.67 (unresolved m, 4H). $^{13}$C NMR ($CDCl_3$): δ 153.40, 152.88, 151.50, 146.67, 140.21, 139.82, 138.76, 133.61, 130.28, 128.89, 126.42, 126.08, 125.54, 125.19, 124.28, 121.43, 121.26, 120.41, 120.28, 55.78, 40.49, 31.63, 29.79, 23.91, 22.71, 14.11. Anal. Calcd for $C_{64}H_{70}N_2S_3Br_2$: C, 68.43; H, 6.28; N, 2.49; S, 8.56. Found: C, 68.06; H, 6.37; N, 2.68; S, 8.76. MS (MALDI-TOF) m/z 1122.47 (M); calcd. for $C_{64}H_{70}N_2S_3Br_2$=1122.31.

Synthesis of N-4

The same above method for the synthesis of N-1 was used. After column chromatography, the product was further purified by thin layer chromatography (TLC) with 1% ethyl acetate in hexane. The product was then recrystallised from hot hexane to give the product as dark red solids (62% yield). $^1$H NMR ($CDCl_3$): δ 8.18 (s, 1H), 8.08 (s, 2H), 7.97 (s, 1H), 7.87 (s, 1H), 7.84-7.75 (m, 3H), 7.71 (s, 1H), 7.61 (d, 1H, J=8.0 Hz), 7.55-7.52 (m, 2H), 2.11 (t, 4H, J=8.0 Hz), 1.16-1.09 (unresolved m, 12H), 0.77 (t, 6H, J=6.4 Hz), 0.73-0.68 (overlapping m, 4H). $^{13}$C NMR (CDCl$_3$): δ 152.94, 152.53, 152.25, 146.51, 144.02, 141.78, 140.31, 138.88, 137.35, 133.88, 132.58, 132.25, 128.95, 127.37, 126.62, 126.15, 125.58, 125.29, 125.03, 124.38, 122.32, 121.70, 120.79, 120.69, 120.42, 55.83, 40.54, 31.62, 29.77, 24.01, 22.67, 14.06. Anal. Calcd for C$_{50}$H$_{76}$N$_2$S$_3$F$_{12}$: C, 69.14; H, 5.51; N, 2.02; S, 6.92. Found: C, 68.17; H, 5.91; N, 2.00; S, 6.18. MS (MALDI-TOF) m/z 1388.45 (M); calcd. for C$_{80}$H$_{76}$N$_2$S$_3$F$_{12}$=1388.50.
Example 3
Synthesis of N-5, N-6, N-7 According to Scheme 3
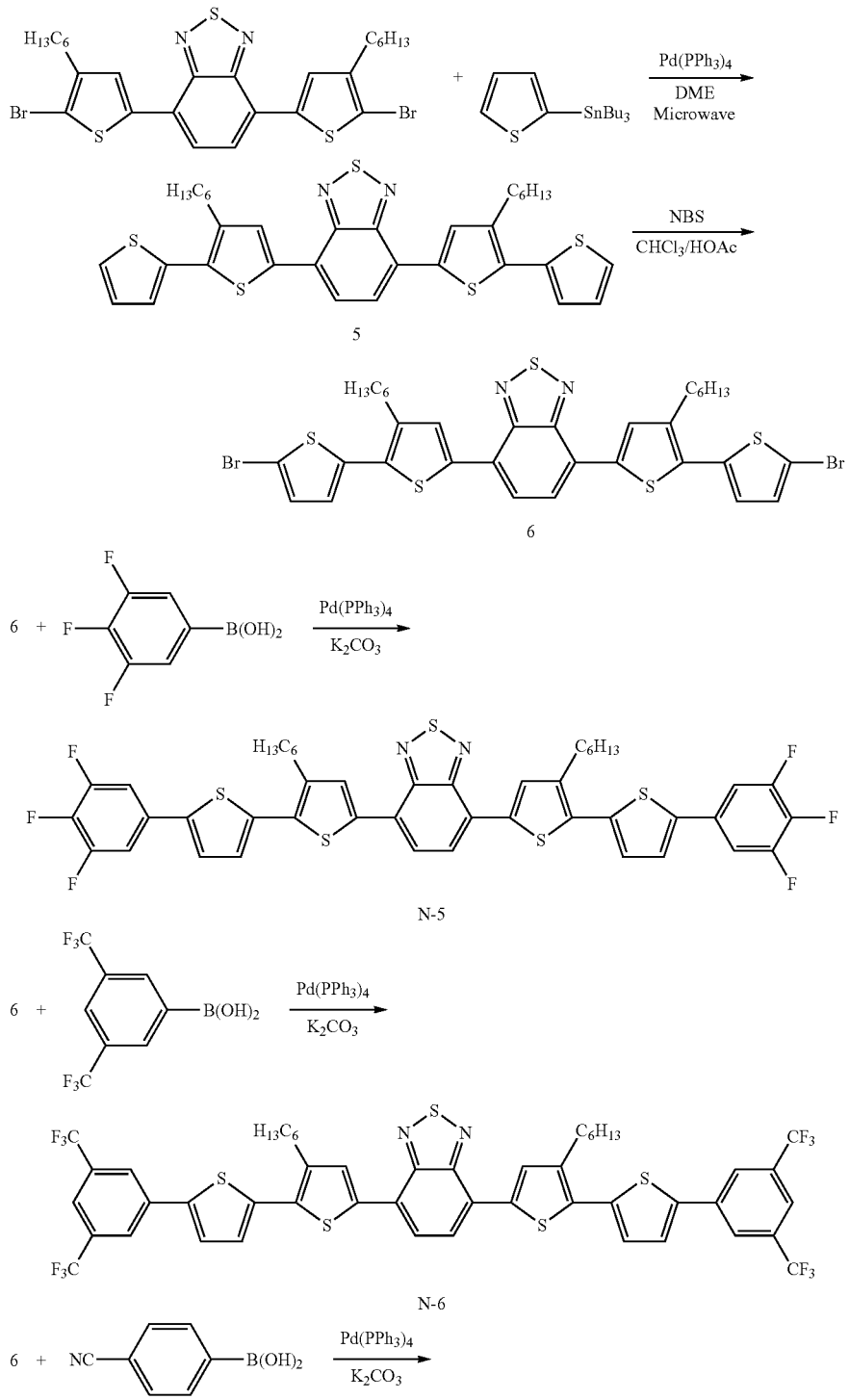

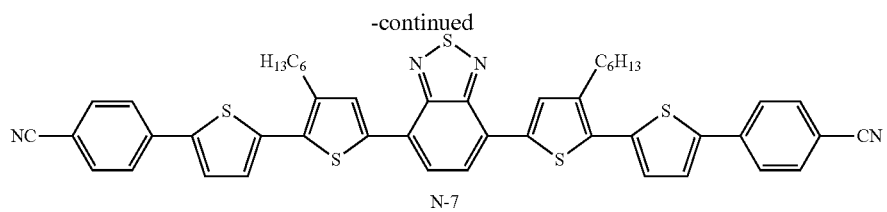

N-7

Synthesis of 5

A 20 mL microwave glass vial was charged with a stirrer bar, 4,7-bis(5-bromo-4-hexylthiophen-2-yl)benzo[c][1,2,5]thiadiazole (0.79 g, 1.3 mmol) and tetrakis(triphenylphosphine)palladium (0) (60 mg, 2 mol %). The vial was purged with nitrogen and sealed. 1,2-dimethoxyethane (16 mL), dimethylformamide (1 mL) and 2-(tributylstannyl)thiophene (0.91 mL, 2.8 mmol) were then added to the vial via syringe. The glass vial was heated in a microwave reactor for 2 minutes at 100° C. and 15 minutes at 150° C. The vial was then cooled and the contents extracted with dichloromethane. The organic layer was dried with MgSO$_4$, concentrated and chromatographed on silica (10% dichloromethane in hexanes) to obtain the title compound (0.66 g, 83%). $^1$H NMR (CDCl$_3$): 7.99 (s, 2H), 7.83 (s, 2H), 7.36 (d, 2H), 7.24 (d, 2H), 7.11 (t, 2H), 2.85 (t, 4H), 1.74 (m, 4H), 1.44-1.33 (m, 12H), 0.89 (t, 6H). MS-MALDI: 632.12 (calc: 632.15).

Synthesis of 6

To a solution of compound 5 (0.8 g, 1.3 mmol) in 100 mL of 1:1 chloroform/glacial acetic acid at 0° C. in the dark was added N-bromosuccinimide (0.49 g, 2.1 equiv) over a period of 20 minutes. The resulting solution was stirred for 4 h and gradually allowed to warm up to room temperature. Water (200 mL) was added and the mixture was extracted 3 times with dichloromethane (100 mL). The organic layer was then washed with water (200 mL), saturated sodium hydrogencarbonate solution (150 mL) and brine (200 mL). It was then dried with MgSO$_4$, concentrated, and recrystallised in ethanol to give the title compound (0.6 g, 60%). $^1$H NMR (CDCl$_3$): 7.63 (s, 2H), 7.83 (s, 2H), 7.06 (d, 2H), 6.96 (s, 2H), 2.80 (t, 4H), 1.70 (m, 4H), 1.43-1.33 (m, 12H), 0.89 (t, 6H). $^{13}$C NMR (CDCl$_3$): 152.5, 141.1, 137.6, 137.4, 131.4, 130.5, 130.3, 126.3, 125.5, 125.3, 112.2, 31.6, 30.6, 29.4, 29.2, 22.6, 14.0. MS-MALDI: 789.95 (calc: 789.97).

Synthesis of N-5

A 25 mL 2-necked round bottom flask equipped with a reflux condenser was charged with 6 (0.32 g, 0.4 mmol), trifluorophenyl boronic acid (0.31 g, 1.2 mmol) and tetrakis(triphenylphosphine)palladium (0) (37 mg, 2 mol %). The flask was flushed with nitrogen, following which toluene (4.5 mL), 2M Na$_2$CO$_3$ (1.5 mL) and ethanol (1.5 mL) were added. The mixture was stirred at 85° C. for 18 h. 50 mg of sodium diethyldithiocarbamate in 1 mL of water was then added and the mixture was stirred overnight at 80° C. It was then cooled, poured into water and extracted with dichloromethane. The organic layer was washed with water and dried with MgSO$_4$, concentrated, chromatographed on silica (5% dichloromethane in hexanes), and recrystallized from dichloromethane/ethanol to give the title compound (220 mg, 61%). $^1$H NMR (CD$_2$Cl$_2$): 8.02 (s, 2H), 7.88 (s, 2H), 7.31 (d, 2H), 7.31-7.23 (m, 8H), 2.89 (t, 4H), 1.80 (m, 4H), 1.49-1.38 (m, 12H), 0.93 (t, 6H). $^{13}$C NMR (CDCl$_3$): 152.8, 152.6, 150.4, 141.1, 140.6, 140.4, 137.4, 137.1, 131.8, 130.7, 127.0, 125.5, 125.3, 124.8, 109.7, 31.7, 30.5, 29.6, 29.3, 22.6, 14.0. MS-MALDI: 892.14 (calc: 892.15).

Synthesis of N-6

A 10 mL microwave glass vial was charged with a stirrer bar, 6 (158 mg, 0.2 mmol), 3,5-bis(trifluoromethyl)benzene boronic acid (155 mg, 0.6 mmol), and dichlorobis(triphenylphosphine)palladium (II) (6 mg, 2 mol %). The vial was purged with nitrogen and sealed. 1,2-dimethoxyethane (0.99 mL), water (0.43 mL) and ethanol (0.23 mL) were then added to the vial via syringe. The glass vial was heated in a microwave reactor for 2 minutes at 100° C. and 15 minutes at 150° C. The vial was then cooled and the contents extracted with dichloromethane. The organic layer was dried with MgSO$_4$, concentrated and chromatographed on silica (5% chloroform in hexanes) to obtain the title compound (55 mg, 26%). $^1$H NMR (CD$_2$Cl$_2$): 8.09 (s, 4H), 8.05 (s, 2H), 7.93 (s, 2H), 7.82 (s, 2H), 7.52 (d, 2H), 7.32 (d, 2H), 2.93 (t, 4H), 1.81 (m, 4H), 1.39-1.27 (m, 12H), 0.93 (t, 6H). MS-MALDI: 1056.32 (calc: 1056.16).

Synthesis of N-7

This compound was synthesized from 6 and 4-cyanophenyl boronic acid using the same procedure as for N-5. The compound was chromatographed on silica (70% chloroform in hexanes) to obtain the title compound in 10% yield. MS-MALDI: 834.28 (calc: 834.20).

Example 4

Synthesis of N-8, N-9, N-10, N-11 According to Scheme 4

Scheme 4

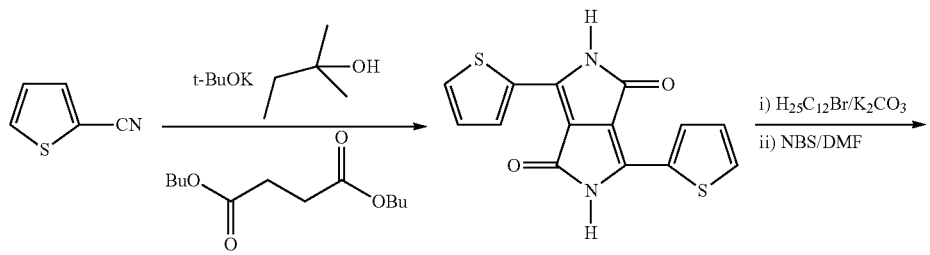

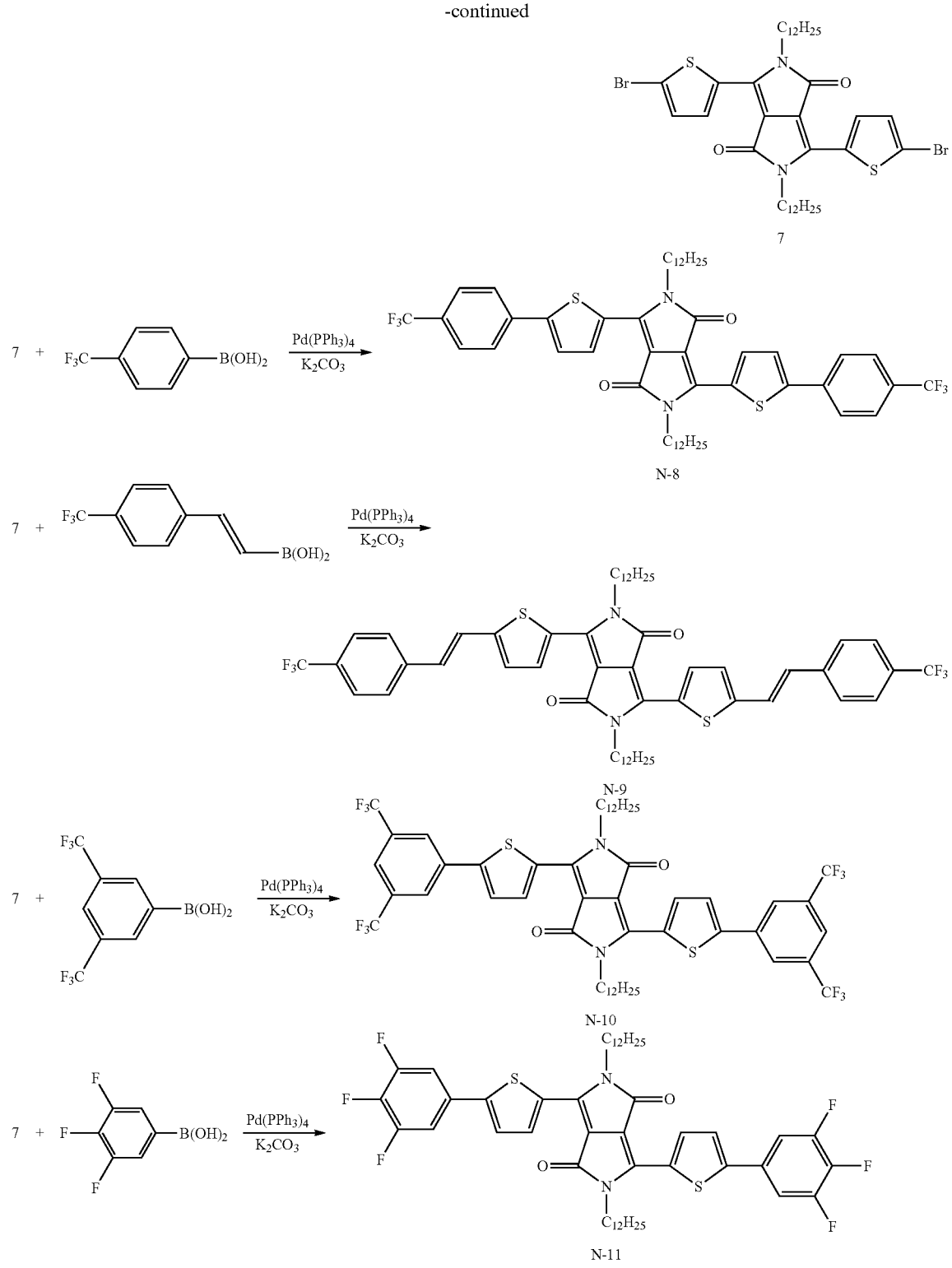

Synthesis of 7

The starting precursor compound, 5-dihydro-1,4-dioxo-3,6-dithienylpyrrolo[3,4-c]-pyrrole (DPP) was synthesized in good yield following a previously reported procedure which contains the reaction of 2-thiophenecarbonitirile with 0.5 eq of di-n-butyl succinate ester and an excess of potassium t-bu-toxide using 2-methyl-2-butanol as solvent. To prepare soluble derivative 3,6-bis-[2,2']bithiophenyl-5-yl-2,5-di-n-dodecylpyrrolo[3,4-c]pyrrole-1,4-dione (DD-DPP). We further did alkylation of DPP using 3 eq of n-dodecylbromide with 3 eq of anhydrous $K_2CO_3$ in presence of anhydrous DMF solvent. Alkylated DPP was additionally dibrominated with N-bromosuccinimide in anhydrous chloroform and crude compound was purified by column chromatography using chloroform as eluent and the overall yield was recorded around 40%. $^1$H NMR (CDCl$_3$): d 0.88 (t, 6H), 1.18-1.47 (m, 36H), 1.75 (m, 4H), 4.09 (t, 4H), 7.29 (d, 2H), 7.65 (d, 4H), 8.94 (d, 2H).

Synthesis of N-8

Dibrominated DD-DPP compound 7 (0.300 g, 0.37 mmol), 4-(trifluoromethyl)phenylboronic acid (0.180 g, 0.94 mmol, 2.5 equiv.) and Pd(PPh$_3$)$_4$ (30 mg, 0.025 mmol) were added to a 50 mL schlenk flask and subjected to three vacuum/argon refill cycles. Argon degassed toluene (15 mL), aqueous 2M K$_2$CO$_3$ (7 mL) and ethanol (3 mL) were added to the above mixture and stirred for 20 min under argon. After three vacuum/argon cycles the mixture was heated at 80° C. for 24 h then monitored via TLC for reaction completion. Toluene was removed using a rotovap and the product extracted with chloroform, then successively washed with water, and dried over MgSO$_4$. Removal of the solvent afforded the crude product which was then purified using column chromatography (silica gel, chloroform as eluent) gives the product as dark purple solid (0.270 g, 78%). $^1$H NMR (CDCl$_3$): δ 0.88 (t, 6H), 1.15-1.47 (m, 36H), 1.80 (t, 4H), 4.09 (t, 4H), 7.52 (d, 2H), 7.65 (d, 4H), 7.78 (d, 4H), 8.93 (d, 2H). MS (MALDI-TOF) m/z 924.57 (M). calcd. for C$_{52}$H$_{62}$F$_6$N$_2$O$_2$S$_2$=924.42.

Synthesis of N-9

Dibrominated DD-DPP compound 7 (0.300 g, 0.37 mmol), trans-2-[4-(trifluoromethyl)phenyl]vinyl-boronic acid (0.204 g, 0.944 mmol, 2.5 equiv.) and Pd(PPh$_3$)$_4$ (30 mg, 0.025 mmol) were added to a 50 mL schlenk flask and subjected to three vacuum/argon refill cycles. Argon degassed toluene (15 mL), aqueous 2M K$_2$CO$_3$ (7 mL) and ethanol (3 mL) were added to the above mixture and stirred for 20 min under argon. After three vacuum/argon cycles the mixture was heated at 80° C. for 24 h then monitored via TLC for reaction completion. Toluene was removed using a rotovap and the product extracted with chloroform, then successively washed with water, and dried over MgSO$_4$. Removal of the solvent afforded the crude product which was then purified using column chromatography (silica gel, chloroform as eluent) gives the product as dark purple crystalline solid (0.250 g, 69%). $^1$H NMR (CDCl$_3$): δ 0.87 (t, 6H), 1.15-1.47 (m, 36H), 1.78 (t, 4H), 4.11 (t, 4H), 7.10-7.15 (d, 2H), 7.28-7.38 (dd, 4H), 7.62 (dd, 8H), 8.92 (d, 2H). MS (MALDI-TOF) m/z 976.47 (M). calcd. for C$_{56}$H$_{66}$F$_6$N$_2$O$_2$S$_2$=976.45.

Synthesis of N-10

Dibrominated DD-DPP compound 7 (0.300 g, 0.37 mmol), 3,5-bis(trifluoromethyl)phenylboronic acid (0.243 g, 0.945 mmol, 2.5 equiv.) and Pd(PPh$_3$)$_4$ (30 mg, 0.025 mmol) were added to a 50 mL schlenk flask and subjected to three vacuum/argon refill cycles. Argon degassed toluene (15 mL), aqueous 2M K$_2$CO$_3$ (7 mL) and ethanol (3 mL) were added to the above mixture and stirred for 20 min under argon. After three vacuum/argon cycles the mixture was heated at 80° C. for 24 h then monitored via TLC for reaction completion. Toluene was removed using a rotovap and the product extracted with chloroform, then successively washed with water, and dried over MgSO$_4$. Removal of the solvent afforded the crude product which was then purified using column chromatography (silica gel, chloroform as eluent) gives the product as dark purple solid (0.200 g, 50%). $^1$H NMR (CDCl$_3$): δ 0.87 (t, 6H), 1.15-1.47 (m, 36H), 1.79 (t, 4H), 4.10 (t, 4H), 7.28-7.31 (s, 1H), 7.52-7.70 (dd, 2H), 7.86 (s, 1H), 8.05 (d, 2H), 8.80-9.00 (dd, 2H). MS (MALDI-TOF) m/z 1060.73 (M). calcd. for C$_{54}$H$_{60}$F$_{12}$N$_2$O$_2$S$_2$=1060.39.

Synthesis of N-11

Dibrominated DD-DPP compound 7 (0.300 g, 0.37 mmol), 3,4,5-trifluorophenylboronic acid (0.243 g, 0.945 mmol, 2.5 equiv.) and Pd(PPh$_3$)$_4$ (30 mg, 0.025 mmol) were added to a 50 mL schlenk flask and subjected to three vacuum/argon refill cycles. Argon degassed toluene (15 mL), aqueous 2M K$_2$CO$_3$ (7 mL) and ethanol (3 mL) were added to the above mixture and stirred for 20 min under argon. After three vacuum/argon cycles the mixture was heated at 80° C. for 24 h then monitored via TLC for reaction completion. Toluene was removed using a rotovap and the product extracted with chloroform, then successively washed with water, and dried over MgSO$_4$. Removal of the solvent afforded the crude product which was then purified using column chromatography (silica gel, chloroform as eluent) gives the product as dark purple crystalline solid (0.240 g, 72%). $^1$H NMR (CDCl$_3$): δ 0.87 (t, 6H), 1.10-1.47 (m, 36H), 1.78 (t, 4H), 4.10 (t, 4H), 7.25 (d, 4H), 7.40 (d, 2H), 8.87 (d, 2H). MS (MALDI-TOF) m/z 896.24 (M). calcd. for C$_{50}$H$_{58}$F$_6$N$_2$O$_2$S$_2$=896.38.

Example 5

Characterization of Compounds N-1 to N-11

The compounds have been characterized by NMR and MALDI-TOF. The thermal properties of the materials have been analyzed by DSC and TGA and the results are presented in Table 1. The materials have melting points ranged from 166 to 231° C., and have high thermal stability (>330° C.) under N$_2$. The photophysical properties of the compounds were measured by UV-vis and fluorescence spectroscopy in toluene. The compounds show strong absorption in 330-700 nm, Cyclic voltammograms in CH$_2$Cl$_2$ were used to determine the HOMO and LUMO characteristics of the materials. The HOMO/LUMO and bandgap values could be tuned in the range from −5.18 to −5.79 eV for HOMOs and −2.98 to −3.55 eV for LUMOs.

Figure 2:
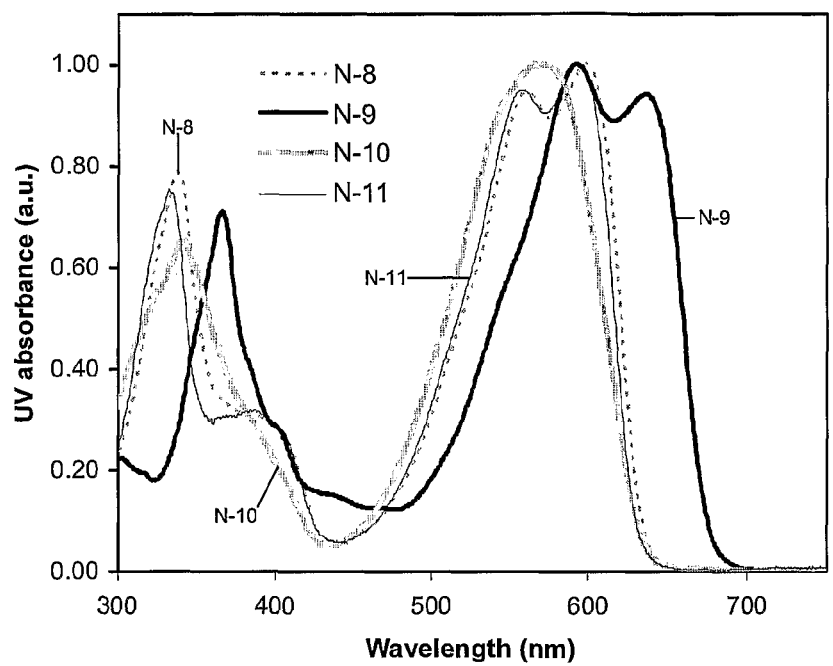
FIG. 2 is a UV absorption spectra from 300 nm to 750 nm for compounds N-8 to N-11 in toluene.

The UV absorption spectra in toluene for compounds N-4 to N-7 are shown in FIG. 1 and for compounds N-8 to N-11 are shown in FIG. 2.

TABLE 1

Physical Properties of N-type Compounds N-1 to N-11

| Compound | Tg (° C.) | T$_m$ (° C.) | T$_d$ (° C.) | HOMO (eV) | LUMO (eV) | Bandgap (eV) | UV$_{max}$ (nm) | UV$_{cutoff}$ (nm) |
|---|---|---|---|---|---|---|---|---|
| N-1 | 62 | 189 | 416 | −5.66 | −2.98 | 2.68 | | |
| N-2 | 60 | 166 | 376 | −5.79 | −3.05 | 2.74 | | |
| N-3 | 79 | 215 | 416 | −5.75 | −3.06 | 2.69 | | |
| N-4 | 82 | / | 426 | −5.35 | −3.27 | 2.08 | 521 | 652 |

TABLE 1-continued

Physical Properties of N-type Compounds N-1 to N-11

| Compound | Tg (° C.) | $T_m$ (° C.) | $T_d$ (° C.) | HOMO (eV) | LUMO (eV) | Bandgap (eV) | $UV_{max}$ (nm) | $UV_{cutoff}$ (nm) |
|---|---|---|---|---|---|---|---|---|
| N-5 | / | 168 | 388 | −5.25 | −3.28 | 1.97 | 509 | 630 |
| N-6 | / | 223 | 379 | −5.28 | −3.31 | 1.97 | 510 | 635 |
| N-7 | / | 258 | 411 | −5.27 | −3.31 | 1.96 | 516 | 637 |
| N-8 | / | 231 | 401 | −5.26 | −3.44 | 1.82 | 599 | 649 |
| N-9 | / | 229 | 390 | −5.18 | −3.49 | 1.69 | 592 | 693 |
| N-10 | / | 208 | 398 | −5.28 | −3.55 | 1.73 | 569 | 648 |
| N-11 | / | 228 | 330 | −5.27 | −3.50 | 1.77 | 595 | 648 |

Example 6

Fabrication and Characterization of Organic Photovoltaic Devices

N-4, N-8, and N-9 have been selected for OPV device fabrication to study the photovoltaic performances of the n-type materials.

Poly(3-hexylthiophene) (P3HT) and selected n-type materials were dissolved in chloroform (weight ratio=1:2) at a total concentration of 10 mg/ml. Patterned ITO-coated glass were used as substrates (with 160 nm of ITO and an average sheet resistance of 14Ω/□). The ITO/glass substrates were cleaned in detergent (30 min), distilled water (10 min, 2 times), acetone (15 mins) and isopropanol (20 min). The substrates were then baked at 100° C. to remove residual solvents. The dried substrates were subjected to oxygen plasma cleaning for 10 min prior to spin coating a 40 nm of PEDOT:PSS hole transporting layer. Subsequently, P3HT:n-type material blends were spin coated on top of the PEDOT:PSS layer with a spinning speed of 1500 rpm for 60 seconds in an inert gas glove box. The metal cathode layer (Ca/Ag) was next evaporated through a shadow mask at a pressure of $8 \times 10^{-5}$ Pa to obtain devices with an active area of 9 mm².

OPV device with configuration of ITO/PEDOT:PSS/P3HT:N-4 (1:2)/Ca/Ag was fabricated. The $V_{oc}$, $J_{sc}$, and fill factor and PCE for the device were measured to be 1.00 V, 3.40 mA/cm², 32% respectively. The power conversion efficiency PCE is 1.10%.

OPV device with configuration of ITO/PEDOT:PSS/P3HT:N-8 (1:2)/Ca/Ag was fabricated. The $V_{oc}$, $J_{sc}$, and fill factor and PCE for the device were measured to be 0.87 V, 1.87 mA/cm², 44% respectively. The power conversion efficiency PCE is 0.72%.

OPV device with configuration of ITO/PEDOT:PSS/P3HT:N-9 (1:2)/Ca/Ag was fabricated. The $V_{oc}$, $J_{sc}$, and fill factor and PCE for the device were measured to be 0.66 V, 1.56 mA/cm², 53% respectively. The power conversion efficiency PCE is 0.55%.

Figure 3:
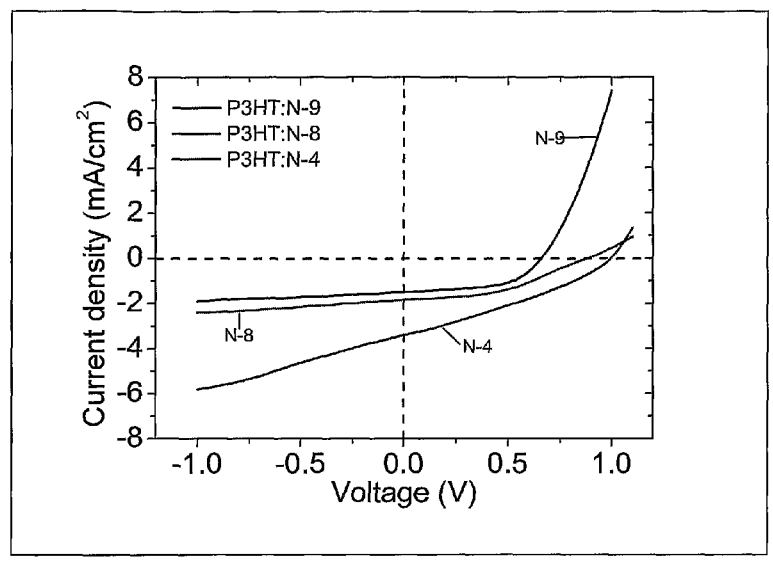
FIG. 3 in and I-V curve for organic photovoltaic devices fabricated with N-4:P3HT (2:1), N-8:P3HT (2:1) and N-9:P3HT (2:1)

The performances of the organic solar cells were characterized under simulated AM1.5G solar irradiation with a power intensity of 100 mW/cm². The photovoltaic performances of P3HT: n-type materials-based organic solar cell are shown in FIG. 3 and key photovoltaic parameters are summarized in Table 2.

From Table 2, it can be seen that OPV devices with power conversion efficiency of 1.1% have been achieved. It is also shown that by fine tuning the LUMO energy levels through selection of the n-type material used, Voc as high as 1.0 V could be achieved.

TABLE 2

Device Performance of Devices with N-4, N-8 or N-9 blended with P3HT

| n-type materials | Voc (V) | Jsc (mA/cm²) | FF (%) | PCE (%) |
|---|---|---|---|---|
| N-4 | 1.00 | 3.40 | 32 | 1.10 |
| N-8 | 0.87 | 1.87 | 44 | 0.72 |
| N-9 | 0.66 | 1.56 | 53 | 0.55 |

All publications and patent applications cited in this specification are herein incorporated by reference as if each individual publication or patent application were specifically and individually indicated to be incorporated by reference. The citation of any publication or patent application is for its disclosure prior to the filing date and should not be construed as an admission that the present invention is not entitled to antedate such publication or patent application by virtue of prior invention.

As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges as given are intended to convey any intermediate value or range contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A compound of formula I:

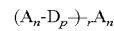

$$(A_n\text{-}D_p\text{-})_r A_n \qquad \text{I}$$

wherein
  each A is an independently selected conjugated electron withdrawing aromatic or heteroaromatic group having from 5 to 50 backbone atoms;
  each A is independently optionally substituted by one or more halo, fluoroalkyl, perfluoroalkyl, carboxyl, cyano, ammonio, nitro, thionyl, sulfonyl, amido linked to the backbone through the oxygen, pyridinium, phosphonium, pyridyl, thiazolyl, oxadiazolyl, triazolyl, alkoxyl, alkylthio, amino, hydroxyl, amido connected to the backbone through the nitrogen, carboxyl connected to the backbone through the oxygen, phenyl, naphthyl, thienyl, furyl, pyrrolyl, carbazolyl, alkyl, alkenyl or alkynyl or any combination thereof, provided that even when substituted the electronic character of each A is electron withdrawing and provided that A is not fluorenonyl;

each D is an independently selected ethenylene group, ethynylene group or a conjugated electron donating aromatic or heteroaromatic group having from 5 to 50 backbone atoms;

each D is independently optionally substituted with one or more alkoxyl, alkylthio, amino, hydroxyl, amido connected to the backbone through the nitrogen, carboxyl connected to the backbone through the oxygen, phenyl, naphthyl, thienyl, furyl, pyrrolyl, carbazolyl, alkyl, alkenyl, alkynyl, halo, fluoroalkyl, perfluoroalkyl, carboxyl, cyano, ammonio, nitro, thionyl, sulfonyl, amido linked to the backbone through the oxygen, pyridinium, phosphonium, pyridyl, thiazolyl, oxadiazolyl or triazolyl or any combination thereof, provided that even when substituted the electronic character of each D is electron donating;

r is an integer having a value of 2 or greater;

each n is independently an integer from 1 to 20;

each p is independently an integer from 1 to 10; and the compound is selected from the group consisting of optionally substituted N-1, N-2, N-3, N-4, N-5, N-6, N-7, N-8, N-9, N-10 and N-11:

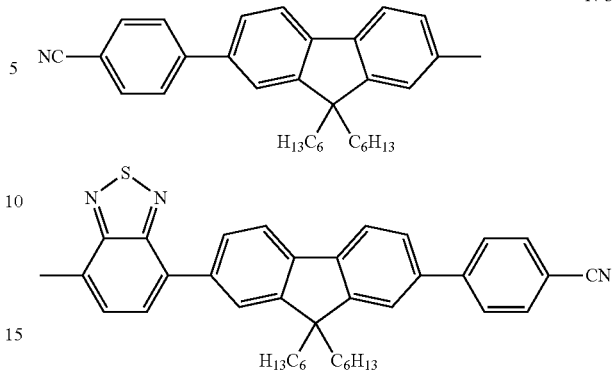

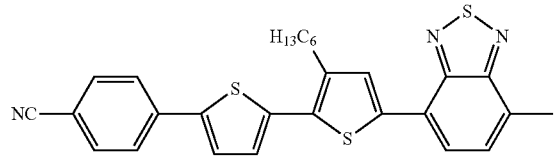
N-7
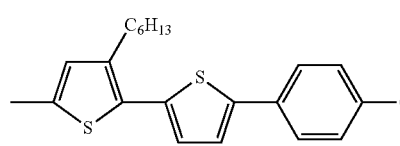
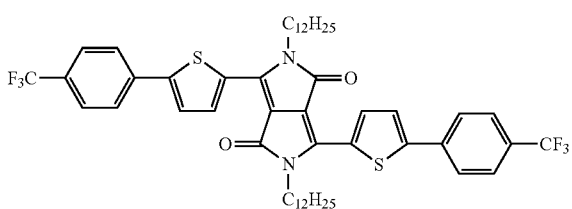
N-8
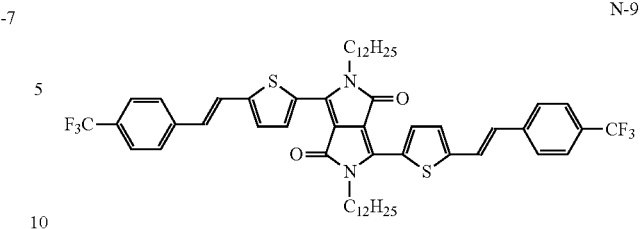
N-9
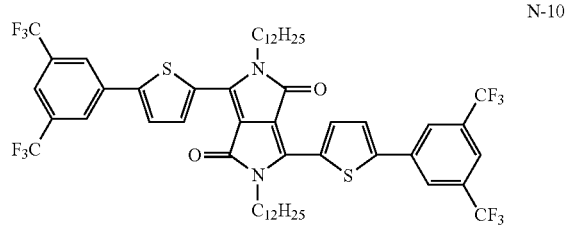
N-10
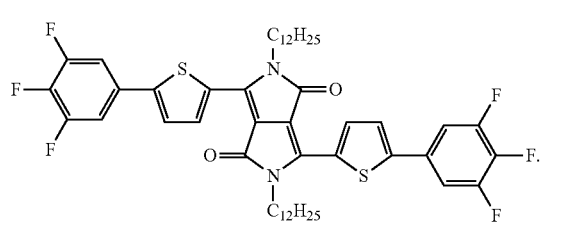
N-11
2. The compound of claim 1 that is N-1, N-2, N-3, N-4, N-5, N-6, N-7, N-8, N-9, N-10 or N-11:
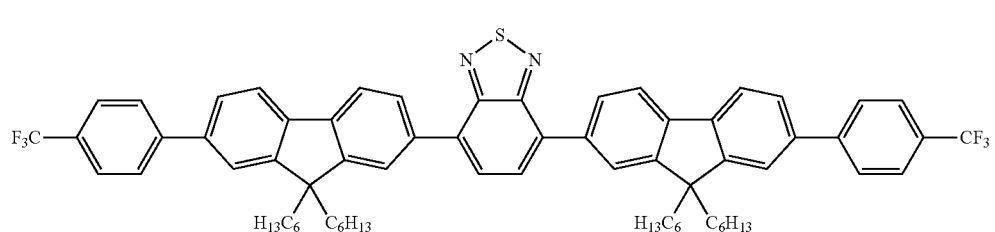
N-1
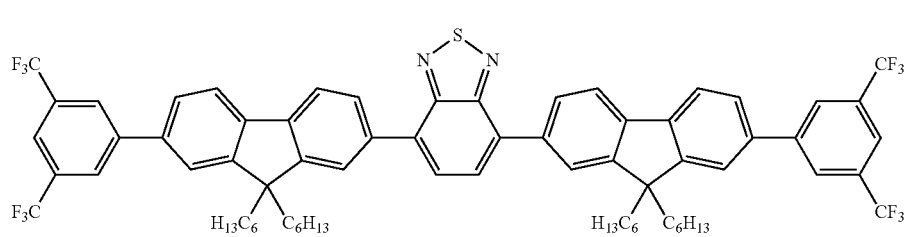
N-2
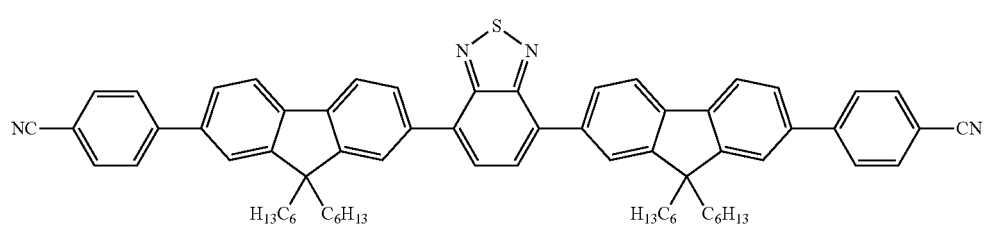
N-3

-continued
N-4
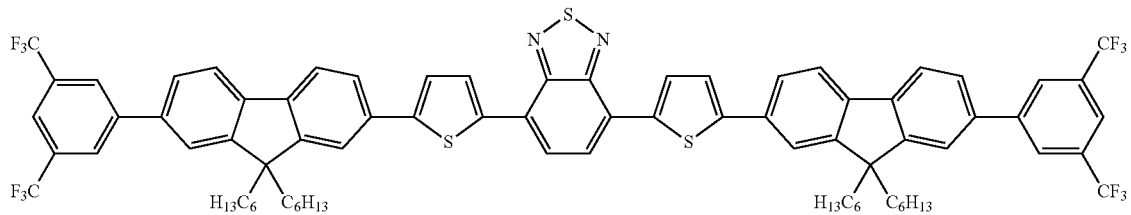
N-5
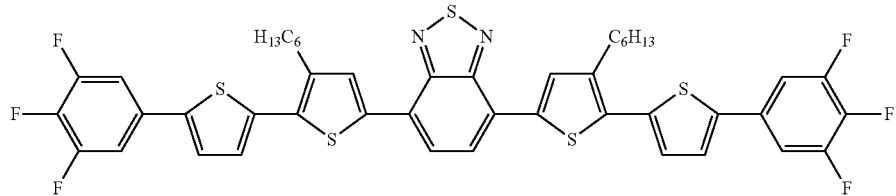
N-6
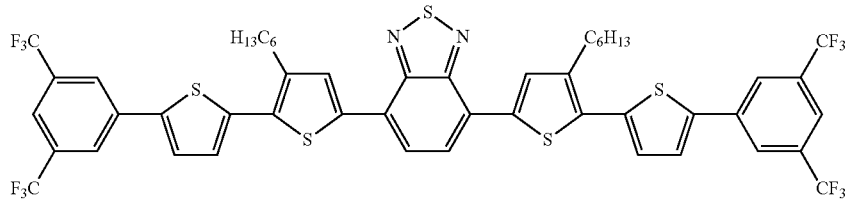
N-7
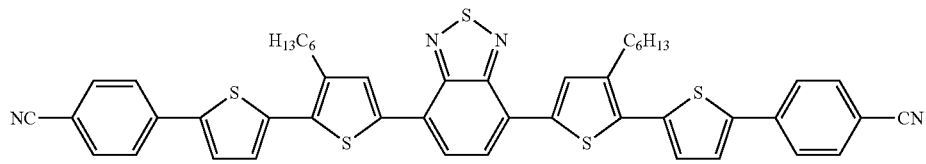
N-8
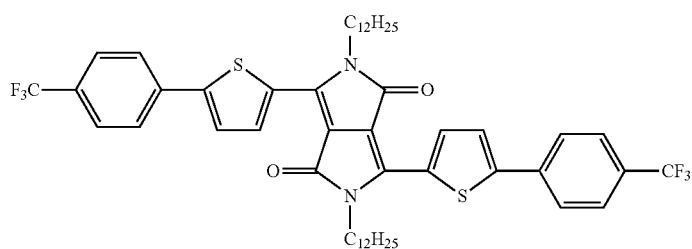
N-9
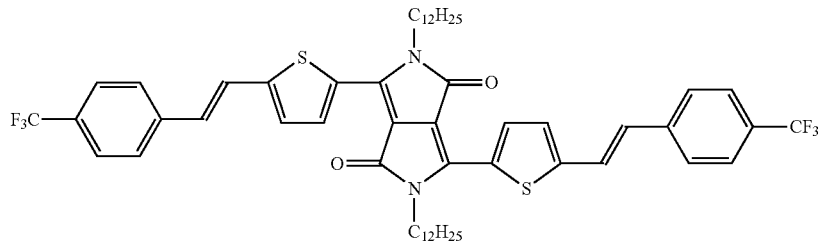
N-10
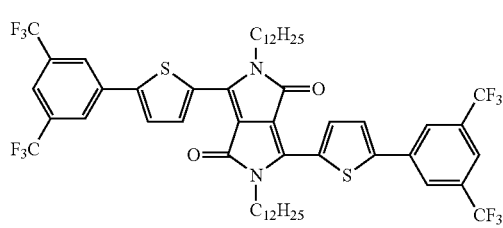
N-11
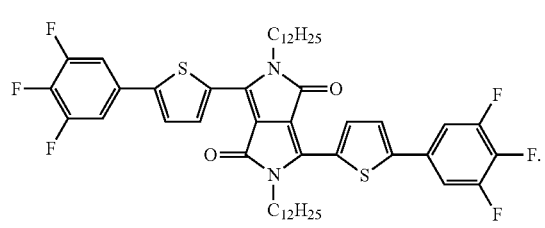

3. A thin film comprising a compound of claim 1.

4. The thin film of claim 3 wherein the thin film further comprises an electron donor material.

5. The thin film of claim 4 wherein the electron donor material comprises regioregular poly(3-hexylthiophene-2,5-diyl) (P3HT), regioregular poly(3-ocylthiophene-2,5-diyl) (P3OT), regioregular poly(quarterthiphene) (PQT), a-poly (phenylene ethynylene)-poly(phenylene vinylene) (A-PPE-PPV), poly[2-methoxy-5-(2'-ethyl-hexyloxy)-1,4-phenylene vinylene] (MEH-PPV), poly[2-methoxy-5-(3,7-dimethyloctyloxy)-1,4-phenylenevinylene] (MDMO-PPV), poly(9,9-dihexyl-fluoren-2,7-diyl-alt-bithiophen-2,5'-diyl), poly(N-alkyl-carbazo-2,7-diyl-alt-4,7-dithienyl-2,1,3-benzothiadiazo-2,5"-diyl), poly[2,6-(4,4-bis(2-ethylhexyl)-4H-cyclopenta[2,1-b:3,4-b']dithiophene)-alt-4,7-(2,1,3-benzothiadiazole)] (PCPDTBT), poly(9,9-dioctyl-silafluoren-2,7-diyl-alt-4,7-dithienyl-2,1,3-benzothiadiazo-2,5"-diyl), or poly[2,6-(4,4-bis(2-ethylhexyl)-4H-cyclopenta[2,1-b:3,4-b']dithiophenesilole)-alt-4,7-(2,1,3-benzothiadiazole)].

6. The thin film of claim 4 wherein the electron donor material comprises P3HT.

7. A device comprising an anode, a cathode and an electron acceptor material comprising a compound of claim 1, the electron acceptor material disposed between the anode and the cathode.

8. The device of claim 7 wherein the electron acceptor material is in a photoactive layer.

9. The device of claim 8 wherein the photoactive layer further comprises an electron donor material.

10. The device of claim 9 wherein the electron donor material comprises regioregular poly(3-hexylthiophene-2,5-diyl) (P3HT), regioregular poly(3-ocylthiophene-2,5-diyl) (P3OT), regioregular poly(quarterthiophene) (PQT), a-poly (phenylene ethynylene)-poly(phenylene vinylene) (A-PPE-PPV), poly[2-methoxy-5-(2'-ethyl-hexyloxy)-1,4-phenylene vinylene] (MEH-PPV), poly[2-methoxy-5-(3,7-dimethyloctyloxy)-1,4-phenylenevinylene] (MDMO-PPV), poly(9,9-dihexyl-fluoren-2,7-diyl-alt-bithiophen-2,5'-diyl), poly(N-alkyl-carbazo-2,7-diyl-alt-4,7-dithienyl-2,1,3-benzothiadiazo-2,5"-diyl), poly[2,6-(4,4-bis(2-ethylhexyl)-4H-cyclopenta[2,1-b:3,4-b']dithiophene)-alt-4,7-(2,1,3-benzothiadiazole)](PCPDTBT), poly(9,9-dioctyl-silafluoren-2,7-diyl-alt-4,7-dithienyl-2,1,3-benzothiadiazo-2,5"-diyl), or poly[2,6-(4,4-bis(2-ethylhexyl)-4H-cyclopenta[2,1-b:3,4-b']dithiophenesilole)-alt-4,7-(2,1,3-benzothiadiazole)].

11. The device of claim 9 wherein the electron donor material comprises P3HT.

12. The device of claim 7 further comprising a smoothing layer disposed between the photoactive layer and the anode, or between the photoactive layer and the cathode.

* * * * *